(12) United States Patent
Keasling et al.

(10) Patent No.: US 7,622,282 B2
(45) Date of Patent: Nov. 24, 2009

(54) BIOSYNTHESIS OF ISOPENTENYL PYROPHOSPHATE

(75) Inventors: Jay D. Keasling, Berkeley, CA (US); Vincent J. J. Martin, Montreal (CA); Douglas J. Pitera, Oakland, CA (US); Seon-Won Kim, Jeongdon-myeon (KR); Sydnor T. Withers, III, Richmond, CA (US); Yasuo Yoshikuni, Berkeley, CA (US); Jack Newman, San Francisco, CA (US); Artem Valentinovich Khlebnikov, Mountain View, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/610,337

(22) Filed: Dec. 13, 2006

(65) Prior Publication Data

US 2007/0099261 A1 May 3, 2007

Related U.S. Application Data

(62) Division of application No. 10/006,909, filed on Dec. 6, 2001, now Pat. No. 7,172,886.

(51) Int. Cl.
*C12P 1/00* (2006.01)
*C12P 7/00* (2006.01)
*C12N 9/00* (2006.01)
*C12N 9/02* (2006.01)
*C12N 9/12* (2006.01)
*C12N 9/88* (2006.01)
*C12N 1/20* (2006.01)
*C12N 15/00* (2006.01)
*C07H 21/04* (2006.01)

(52) U.S. Cl. .................. 435/132; 435/41; 435/183; 435/189; 435/194; 435/232; 435/252.3; 435/320.1; 536/23.2

(58) Field of Classification Search .............. 435/41, 435/132, 183, 189, 194, 232, 252.3, 320.1; 536/23.2
See application file for complete search history.

(56) References Cited

U.S. PATENT DOCUMENTS

| | | | |
|---|---|---|---|
| 6,072,045 | A | 6/2000 | Chappell et al. |
| 6,114,160 | A | 9/2000 | Croteau et al. |
| 6,190,895 | B1 | 2/2001 | Croteau et al. |
| 6,281,017 | B1 | 8/2001 | Croteau et al. |
| 6,284,506 | B1 | 9/2001 | Hoshino et al. |
| 6,291,745 | B1 | 9/2001 | Meyer et al. |
| 6,306,633 | B1 | 10/2001 | Wilding et al. |
| 6,495,354 | B2 | 12/2002 | Chappell et al. |
| 6,531,303 | B1 | 3/2003 | Mills et al. |
| 6,916,972 | B2 | 7/2005 | Falco et al. |
| 6,989,257 | B2 | 1/2006 | Berry et al. |
| 7,129,392 | B2 | 10/2006 | Hahn et al. |
| 7,132,268 | B2 | 11/2006 | Miyake et al. |
| 2004/0029239 | A1 | 2/2004 | Ohto et al. |
| 2004/0063182 | A1 | 4/2004 | Ohto et al. |
| 2005/0241017 | A1 | 10/2005 | Hahn et al. |
| 2005/0266518 | A1 | 12/2005 | Berry et al. |

FOREIGN PATENT DOCUMENTS

| | | |
|---|---|---|
| EP | 0955363 | 11/1999 |
| EP | 1360300 | 11/2003 |
| EP | 1392824 | 3/2004 |
| WO | WO 0210398 | 2/2002 |
| WO | WO 02099095 | 12/2002 |
| WO | WO 2000001650 | 1/2005 |

OTHER PUBLICATIONS

Takagi et al. J Bacteriol. Aug. 2000;182(15):4153-7.*
Berges et al. Accession X97557. Oct. 29, 1997.*
Balbas et al. Gene. Jun. 12, 1996;172(1):65-9.*
Oulmouden et al. Accession X55875. Feb. 20, 1991.*
Skelton et al. Accession Z49939. Jun. 29, 1995.*
Kajiwara et al. Biochem J. Jun. 1, 1997;324 (Pt 2):421-6.*
Zhu et al. (Plant Cell Physiol. Mar. 1997;38(3):357-61.*
Wilding et al. J Bacteriol. Aug. 2000;182(15):4319-27.*
Hinson et al. J Lipid Res. Nov. 1997;38(11):2216-23.*
Sahdev et al. Production of active eukaryotic proteins through bacterial expression systems: a review of the existing biotechnology strategies. (2008) Mol. Cell Biochem. 307:249.
Altincicek et al., "GcpE is Involved in the 2-C-Methyl-D-Erythritol 4-Phosphate Pathway of Isoprenoid Biosynthesis in *Escherichia coli*" (2001) Journal of Bacteriology, vol. 183, No. 8, pp. 2411-2416.
Amann et al., Tightly Regulated Tac Promoter Vectors Useful for the Expression of Unfused and Fused Proteins in *Escherichia coli* , (1988), Gene, vol. 69, pp. 301-315.
Balbas et al., (1996), Gene, vol. 172, No. 1, pp. 65-69.
Barkovich et al., "Metabolic Engineering of Isoprenoids" (2001), Metabolic Engineering, vol. 3, No. 1, pp. 27-39.
Campos et al., Identification of gcpE as a Novel Gene of the 2-C-Methyl-D-Erythritol 4-Phosphate Pathway for Isoprenoid Biosnythesis in *Escherichia coli*, (2001), FEBS Letters, vol. 488, pp. 170-173.
Campos et al., *Escherichia coli* Engineered to Synthesize Isopentenyl Diphosphate and Dimethylallyl Diphosphate from Mevalonate: A Novel System for the Genetic Analysis of the 2-C-Methyl-D-Erythritol 4-Phosphate Pathway for Isoprenoid Biosynthesis (2001) Biochemistry Journal, vol. 353, pp. 59-67.

(Continued)

*Primary Examiner*—Christian L Fronda
(74) *Attorney, Agent, or Firm*—Paula A. Borden; Bozicevic, Field & Francis LLP

(57) ABSTRACT

Methods for synthesizing isopentenyl pyrophosphate are provided. A first method comprises introducing into a host microorganism a plurality of heterologous nucleic acid sequences, each coding for a different enzyme in the mevalonate pathway for producing isopentenyl pyrophosphate. A related method comprises introducing into a host microorganism an intermediate in the mevalonate pathway and at least one heterologous nucleic acid sequence, each sequence coding for an enzyme in the mevalonate pathway necessary for converting the intermediate into isopentenyl pyrophosphate. The invention also provides nucleic acid sequences, enzymes, expression vectors, and transformed host cells for carrying out the methods.

41 Claims, 5 Drawing Sheets

OTHER PUBLICATIONS

Cunningham et al., "Molecular Structure and Enzymatic function of Lycopene Cyclase from the *Cyanobacterium synechococcus* sp Strain PCC7942," (1994) The Plant Cell, vol. 6, pp. 1107-1121.

Dairi et al., Eubacterial Diterpene Cyclase Genes Essential for Production of the Isoprenoid Antibotic Terpentecin (2001), Journal of Bacteriology, vol. 183, No. 20, pp. 6085-6094.

Guzman et al, Tight Regulation, Modulation, and High-Level Expression by Vectors Containing the Arabinose $P_{BAD}$ Promoter, (1995), Journal of Bacteriology, vol. 177, No. 14, pp. 4121-4130.

Hahn et al., "*Escherichia coli* Open Reading Frame 696 Is idi, a Nonessential Gene Encoding Isopentenyl Diphosphate Isomerase," (1999), Journal of Bacteriology, vol. 181, No. 15, pp. 4499-4504.

Hahn et al, "I-Deoxy-D-Xylulose 5-Phosphate Synthase, the Gene Product of Open Reading Frame (ORF) 2816 and ORF 2895 in *Rhodobacter capsulatus*" (2001), Journal of Bacteriology, vol. 183, No. 1, pp. 1-11.

Hamano et al., Cloning of a Gene Cluster encoding Enzymes Responsible for the Mevalonate Pathway from a Terpenoid-Antibioltic-Producing *Streptomyces* Strain, (2001), Biosci Biotechnol. Biochem. vol. 65, No. 7, pp. 1627-1635.

Kaneda et al., "An Unusual Isopentenyl Diphosphase Isomerase Found in the Mevalonate Pathway Gene Cluster from *Streptomyces* sp. Strain CL 190" (2001), PNAS, vol. 98, No. 3, pp. 932-937.

Kim et al., "Metabolic Engineering of the Nonmevalonate Isopentenyl diphosphate Synthesis Pathway in *Escherichia coil* Enhances Lycopene Production" (2001), Biotechnology and Bioengineering, vol. 72, No. 4, pp. 408-415.

Kovach et al., "pBBRIMCS: A Broad-Host-Range Cloning Vector" (1994), BioTechniques, vol. 16, No. 5, pp. 800-802.

Kovach et al., Four New Derivatives of the Broad-Host-Range-Cloning Vector pBBRIMCS. Carrying Different Antibiotic-Resistance Cassettes, (1995), Gene, vol. 166, pp. 175-176.

Mahmoud et al., "Metabolic Engineering of Essential Oil Yield and Composition in Mint by Altering Expression of Deoxyxylulose Phosphate Reductoisomerase and Methofuran Synthase", (2001), PNAS, vol. 98, No. 15, pp. 8915-8920.

McAteer et al., "The lytb Gene of *Escherichia coli* Is Essential and Specifies a Product Needed for Isoprenoid Biosyntheis" (2001), Journal of Bacteriology, vol. 183, No. 24, pp. 7403-7407.

Oulmouden et al., "Nucleotide Sequence of the ERG12 Gene of *Saccharomyces cerevisae* Encoding Mevalonate Kinase" (1991), Current Genetics, vol. 19, pp. 9-14.

Polakowski et al., "Overexpression of a Cytosolic Hydroxymethylglutaryl-CoA Reductase Leads to Squalene Accumulation in Yeast", (1998), Appl. Microbiol. Biotechnol., vol. 49, pp. 66-71.

Rohdich et al., Studies on the Nonmevalonate Terpene Biosynthetic Pathway: Metabolic Role of IspH (LyB) Protein, (2002), PNAS, vol. 99, No. 3, pp. 1158-1163.

Rohlin et al., "Microbioal Pathway Engineering for Industrial Processes: Evolution, Combinatorial Biosynthesis and Rational Design" (2001), Current Opinion in Microbiology, vol. 4, pp. 330-335.

Rohmer et al., "Isoprenoid Biosynthesis in Bacteria: A Novel Pathway for the Early Steps Leading to Isopentenyl Diphosphate", (1993), Biochem. J., vol. 295, pp. 517-524.

Sandmann, "Carotenoid Biosynthesis and Biotechnological Application" (2001), Archives of Biochemistry and Biophysics, vol. 385, pp. 4-12.

Szkopinska et al., "The Regulation of Activity of Main Mevalonic Adic Pathway Enzymes: Farnesyl Diphosphas Synthase. 3-Hydroxy-3-Methylglutaryl-CoA Reductase, and Squalene Synthase in Yeast *Saccharomyces cerevidiae*", (2000), Biochemical and Biophysical Research Communications, vol. 267, pp. 473-477.

Takagi et al., "A Gene Cluster for the Mevalonate Pathway from *Streptomyces* sp. Strain CL 190." (2000), Journal of Bacteriology, vol. 182, No. 15, pp. 4153-4157.

Tatiana et al., FEMS Microbiol Lett (1999), May 15, vol. 174, No. 2, pp. 247-250.

Toth et al., "Molecular Cloning and Expression of the cDNAs Encoding Human and Yeast Mevalonate Pyrophosphate Decarboxylase", (1996), The Journal of Biological Chemistry, vol. 271, No. 14, pp. 7895-7898.

Tsay et al., "Cloning and Characterization of ERG8, an Essential Gene of *Saccharomyces cervisiae* that Encodes Phosphomevalonate Kinase", (1991), Molecular and Cellular Biology, vol. 11, No. 2, pp. 620-631.

Wang et al., "Engineered Isoprenoid Pathway Enhances Astaxanthin Production in *Escherichia coli*", (1999), Biotechnology and Bioengineering, vol. 62, No. 2, pp. 235-241.

Wang et al., Directed Evolution of Metabolically Engineered *Escherichia coli* for Carotenoid Production, (2000), Biotechnol. Prod., vol. 16, No. 6, pp. 922-926.

66 FR 1099, Friday, Jan. 5, 2001.

BLAST 2 Sequences results. Sequence 1 gi 5531936, Sequence 2 gi 546900, printed on Jun. 24, 2005.

Hiser et al., "ERG10 from *Saccharomyces cerevisiae* Encodes Acetoacetyl-CoA Thiolase" (1994), Journal of Biological Chemistry, vol. 269, No. 50, pp. 31383-31389.

Hiser et al., Accession L20428, Feb. 23, 1995.

National Science Foundation Award Abstract No. 9911463, Feb. 10, 2006.

Fujisaki et al., (1986) Journal Biochemistry, vol. 99, No. 5, pp. 1327-1337.

* cited by examiner

BIOSYNTHESIS OF ISOPENTENYL PYROPHOSPHATE

CROSS-REFERENCE

This application is a divisional application of U.S. patent application Ser. No. 10/006,909, filed Dec. 6, 2001 now U.S. Pat. No. 7,172,886, which is incorporated herein by reference in its entirety and to which application priority is claimed under 35 USC § 120.

TECHNICAL FIELD

The present invention relates to the biosynthesis of isopentenyl pyrophosphate (IPP) and isoprenoids derived therefrom. More particularly, the invention relates to methods for biosynthesizing isopentenyl pyrophosphate, and to nucleic acid sequences, enzymes, expression vectors, and transformed host cells for carrying out the methods.

BACKGROUND

Isoprenoids are compounds derived from the five-carbon molecule, isopentenyl pyrophosphate. Investigators have identified over 29,000 individual isoprenoid compounds, with new ones continuously being discovered. Isoprenoids are often isolated from natural products, such as plants and microorganisms, which use isopentenyl pyrophosphate as a basic building block to form relatively complex structures. Vital to living organisms, isoprenoids serve to maintain cellular fluidity and electron transport, as well as function as natural pesticides, to name just a few of their roles in vivo. Furthermore, the pharmaceutical and chemical communities use isoprenoids as pharmaceuticals, nutriceuticals, flavoring agents, and agricultural pest control agents. Given their importance in biological systems and usefulness in a broad range of applications, isoprenoids have been the focus of much attention by scientists.

Conventional means for obtaining isoprenoids include extraction from biological materials (e.g., plants, microbes, and animals) and partial or total organic synthesis in the laboratory. Such means, however, have generally proven to be unsatisfactory. For example, organic synthesis is usually complex since several steps are required to obtain the desired product. Furthermore, these steps often involve the use of toxic solvents, which require special handling and disposal. Extraction of isoprenoids from biological materials may also require toxic solvents. In addition, extraction and purification methods usually provide a low yield of the desired isoprenoid, as biological materials typically contain only small quantities of these compounds. Unfortunately, the difficulty involved in obtaining relatively large amounts of isoprenoids has limited their practical use. In fact, the lack of readily available methods by which to obtain certain isoprenoids has slowed down the progression of drug candidates through clinical trials. Furthermore, once an isoprenoid drug candidate has passed the usual regulatory scrutiny, the actual synthesis of the isoprenoid drug may not lend itself to a commercial scale.

As a solution to such problems, researchers have looked to biosynthetic production of isoprenoids. Some success has been obtained in the identification and cloning of the genes involved in isoprenoid biosynthesis. For example, Meyer et al. U.S. Pat. No. 6,291,745 describes the production of limonene and other metabolites in plants. Although many of the genes involved in isoprenoid biosynthesis may be expressed in functional form in *Escherichia coli* and other microorganisms, yields remain relatively low as a result of minimal amounts of precursors, namely isopentenyl pyrophosphate.

In an effort to address the lack of isopentenyl pyrophosphate, some investigators have attempted to increase isopentenyl pyrophosphate production. Croteau et al. describe in U.S. Pat. No. 6,190,895 the nucleic acid sequences that code for the expression of 1-deoxyxylulose-5-phosphate synthase, an enzyme used in one biological pathway for the synthesis of isopentenyl pyrophosphate. Low yields of isopentenyl pyrophosphate remain, however, since several more enzymes are needed to catalyze other steps in this isopentenyl pyrophosphate biosynthetic pathway. Further, the reference does not address an alternative pathway for isopentenyl pyrophosphate biosynthesis, namely the mevalonate pathway.

Thus, the current invention is directed toward solving these and other disadvantages in the art by increasing the typically low yields associated with conventional synthesis of isopentenyl pyrophosphate and isoprenoids. Specifically, the current invention is directed toward identification of new methods for the synthesis of isopentenyl pyrophosphate, as isopentenyl pyrophosphate represents the universal precursor to isoprenoid synthesis.

SUMMARY OF THE INVENTION

Accordingly, it is an object of the present invention to overcome the above-mentioned disadvantages of the prior art by providing a method for synthesizing isopentenyl pyrophosphate in a host microorganism, comprising the step of introducing into the host microorganism a plurality of heterologous nucleic acid sequences, each coding for a different enzyme in the mevalonate pathway for producing isopentenyl pyrophosphate.

It is another object of the invention to provide such a method wherein the plurality of heterologous nucleic acid sequences is contained in at least one extrachromosomal expression vector.

It is still another object of the invention to provide such a method wherein the isopentenyl pyrophosphate is further synthesized into an isoprenoid.

It is yet another object of the invention to provide such a method wherein the isoprenoid is selected from the group consisting of a monoterpene, sesquiterpene, diterpene, sesterterpene, triterpene, tetraterpene, and a steroid.

It is a further object of the invention to provide such a method wherein the plurality of heterologous nucleic acid sequences further comprises a DNA fragment coding for an enzyme capable of converting isopentenyl pyrophosphate to dimethylallyl pyrophosphate.

It is still a further object of the invention to provide a method wherein the host microorganism is a prokaryote.

It is an additional object of the invention to provide a method wherein the prokaryote is *Escherichia coli*.

Is it still another object of the invention to provide a method for synthesizing isopentenyl pyrophosphate in a host microorganism, wherein the method comprises introducing into the host microorganism an intermediate in the mevalonate pathway and at least one heterologous nucleic acid sequence, each said sequence coding for an enzyme in the mevalonate pathway necessary for converting the intermediate into isopentenyl pyrophosphate.

It is still a further object of the invention to provide DNA fragments, expression vectors, and host cells for carrying out the methods described herein.

Additional objects, advantages, and novel features of the invention will be set forth in part in the description that follows, and in part will become apparent to those skilled in the art upon examination of the following, or may be learned through routine experimentation upon practice of the invention.

In one embodiment, the invention provides a method for synthesizing isopentenyl pyrophosphate in a host microorganism. The method comprises introducing into a host microorganism a plurality of heterologous nucleic acid sequences, each coding for a different enzyme in the mevalonate pathway for producing isopentenyl pyrophosphate. As will be appreciated by those skilled in the art, the mevalonate pathway involves six enzymes. The pathway starts from acetyl-CoA, proceeds through the intermediate mevalonic acid, and results in isopentenyl pyrophosphate. Of course, additional nucleotide sequences coding for other genes may be introduced as well. In particular, nucleotide sequences coding for enzymes necessary in the production of specific isoprenoids may be introduced into the host microorganism, along with those coding for enzymes in the mevalonate pathway. Preferably, at least one extrachromosomal expression vector will be used to introduce the desired nucleic acid sequence(s), although more than one (e.g., two) different expression vectors may be used. In addition, the desired nucleic acid sequence(s) may be incorporated into the host microorganism's chromosomal material.

In another embodiment, the invention provides a method for synthesizing isopentenyl pyrophosphate in a host microorganism by introducing into the host microorganism an intermediate of the mevalonate pathway and one or more heterologous nucleic acid sequences. The introduced sequence or sequences each code for an enzyme in the mevalonate pathway necessary for converting the intermediate into isopentenyl pyrophosphate. Thus, for example, if mevalonate is the introduced intermediate, the method requires introduction of nucleic acid sequences that code for the enzymes necessary to convert mevalonate into isopentenyl pyrophosphate, for example, the introduction of nucleic acid sequences coding for an enzyme that phosphorylates mevalonate to mevalonate 5-phosphate, an enzyme that converts mevalonate 5-phosphate to mevalonate 5-pyrophosphate, and an enzyme that converts mevalonate 5-pyrophosphate to isopentenyl pyrophosphate. Of course, other intermediates in the mevalonate pathway, along with the necessary nucleic acid sequences, may be introduced as well.

Although any host microorganism, e.g., a prokaryote or eukaryote, may be employed, it is preferred that a prokaryote such as Escherichia coli be used. Preferably, the host organism does not synthesize isopentenyl pyrophosphate through the mevalonate pathway, but rather through the deoxyxylulose-5 phosphate (DXP) pathway. In this way, side reactions involving the intermediates of the mevalonate pathway are minimized, thereby enhancing the yield and efficiency of the present methods.

In another embodiment of the invention, DNA fragments, each coding for an enzyme in the mevalonate pathway, are provided in one or more expression vectors. Thus, for the mevalonate pathway, the DNA fragments include those that code for enzymes capable of: (a) condensing two molecules of acetyl-CoA to acetoacetyl-CoA, preferably the nucleotide sequence of SEQ ID NO 1; (b) condensing acetoacetyl-CoA with acetyl-CoA to form HMG-CoA, preferably the nucleotide sequence of SEQ ID NO 2; (c) converting HMG-CoA to mevalonate, preferably the nucleotide sequence of SEQ ID NO 3; (d) phosphorylating mevalonate to mevalonate 5-phosphate, preferably the nucleotide sequence of SEQ ID NO 4; (e) converting mevalonate 5-phosphate to mevalonate 5-pyrophosphate, preferably the nucleotide sequence of SEQ ID NO 5; and (f) converting mevalonate 5-pyrophosphate to isopentenyl pyrophosphate, preferably the nucleotide sequence of SEQ ID NO 6.

In yet another embodiment, the invention provides expression vectors comprising the DNA fragments described above and elsewhere in the application, as well as host cells transformed with such expression vectors. The DNA fragments, expression vectors, and host cells transformed with the same expression vectors are useful in the present methods for synthesizing isopentenyl pyrophosphate.

BRIEF DESCRIPTION OF THE DRAWINGS

For reference.

DETAILED DESCRIPTION OF THE INVENTION

Figure 1A:
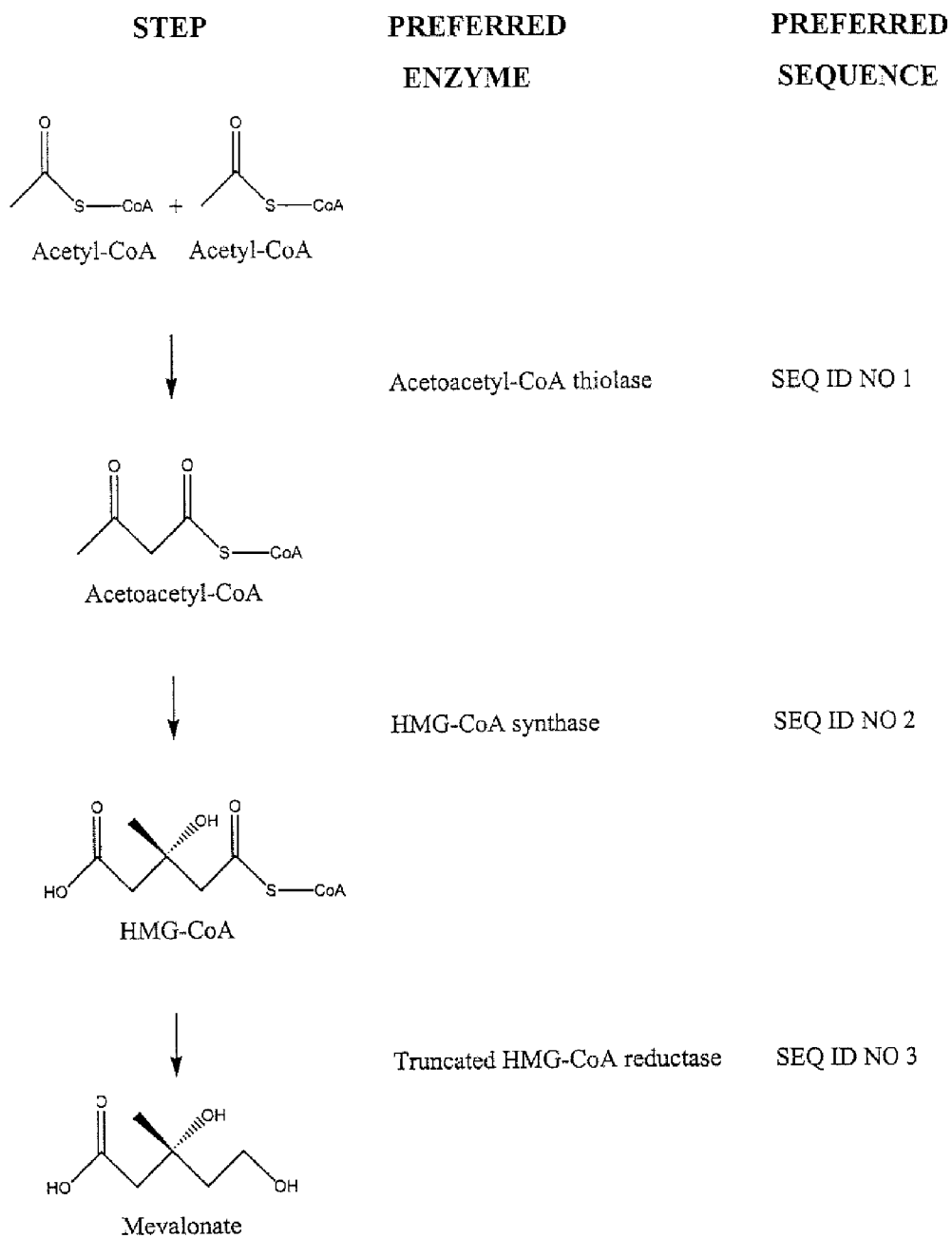
FIGS. 1A and 1B schematically illustrate the mevalonate pathway of isopentenyl pyrophosphate synthesis, along with enzymes involved and nucleic acid sequences coding for such enzymes.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host microorganism" and "cell" are used interchangeably herein to refer to a living biological cell that can be transformed via insertion of an expression vector. Thus, a host organism or cell as described herein may be a prokaryotic organism (e.g., an organism of the kingdom Bubacteria) or a eukaryotic cell. As will be appreciated by one of ordinary skill in the art, a prokaryotic cell lacks a membrane-bound nucleus, while a eukaryotic cell has a membrane-bound nucleus. A preferred prokaryotic cell is *Escherichia coli*. Preferred eukaryotic cells are those derived from fungal, insect, or mammalian cell lines.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The term "mevalonate pathway" is used herein to refer to the pathway that converts acetyl-CoA to isopentenyl pyrophosphate through a mevalonate intermediate.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IJUPAC-IUB Commission of Biochemical Nomenclature (*Biochemistry* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

In a first embodiment, the invention provides a method for synthesizing isopentenyl pyrophosphate, the fundamental building block of isoprenoids, in a host microorganism.

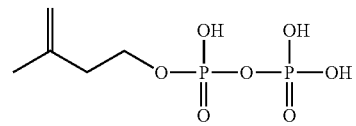

Isopentenyl pyrophosphate

Isopentenyl pyrophosphate is also known as "isopentenyl diphosphate" and is commonly abbreviated as "IPP." The method comprises introducing into the host microorganism a plurality of heterologous nucleic acid sequences each coding for a different enzyme in the mevalonate pathway for producing isopentenyl pyrophosphate. As stated previously, the mevalonate pathway for producing isopentenyl pyrophosphate in living organisms begins with acetyl-CoA and involves a mevalonate intermediate.

In another method for synthesizing isopentenyl pyrophophate, an intermediate in the mevalonate pathway is introduced into the host microorganism. Although any method for introducing the intermediate may be used, it is preferred to add the intermediate to the culture medium used to grow the host microorganism. In this way, the intermediate is transported, e.g., via passive diffusion, across the cellular membrane and into the host microorganism.

Either before or after the intermediate is introduced, nucleic acid sequence(s) are introduced that code for those enzymes of the mevalonate pathway necessary to convert the intermediate into isopentenyl pyrophosphate. As will be appreciated by one of ordinary skill in the art, the conversion from the intermediate into isopentenyl pyrophosphate may require one, two, three, or more steps. Although any of the intermediates, i.e., acetyl Co-A, acetoacetyl-CoA, HMG-CoA, mevalonate, mevalonate 5-phosphate, and mevalonate 5-diphosphate, may be used, introduction of DL-mevalonate is a particularly preferred intermediate when using this method in the production of isopentenyl pyrophosphate. Enantiomers of any of the intermediates, such as the bioactive enantiomer D-mevalonate, may be used as well.

Figure 1B:
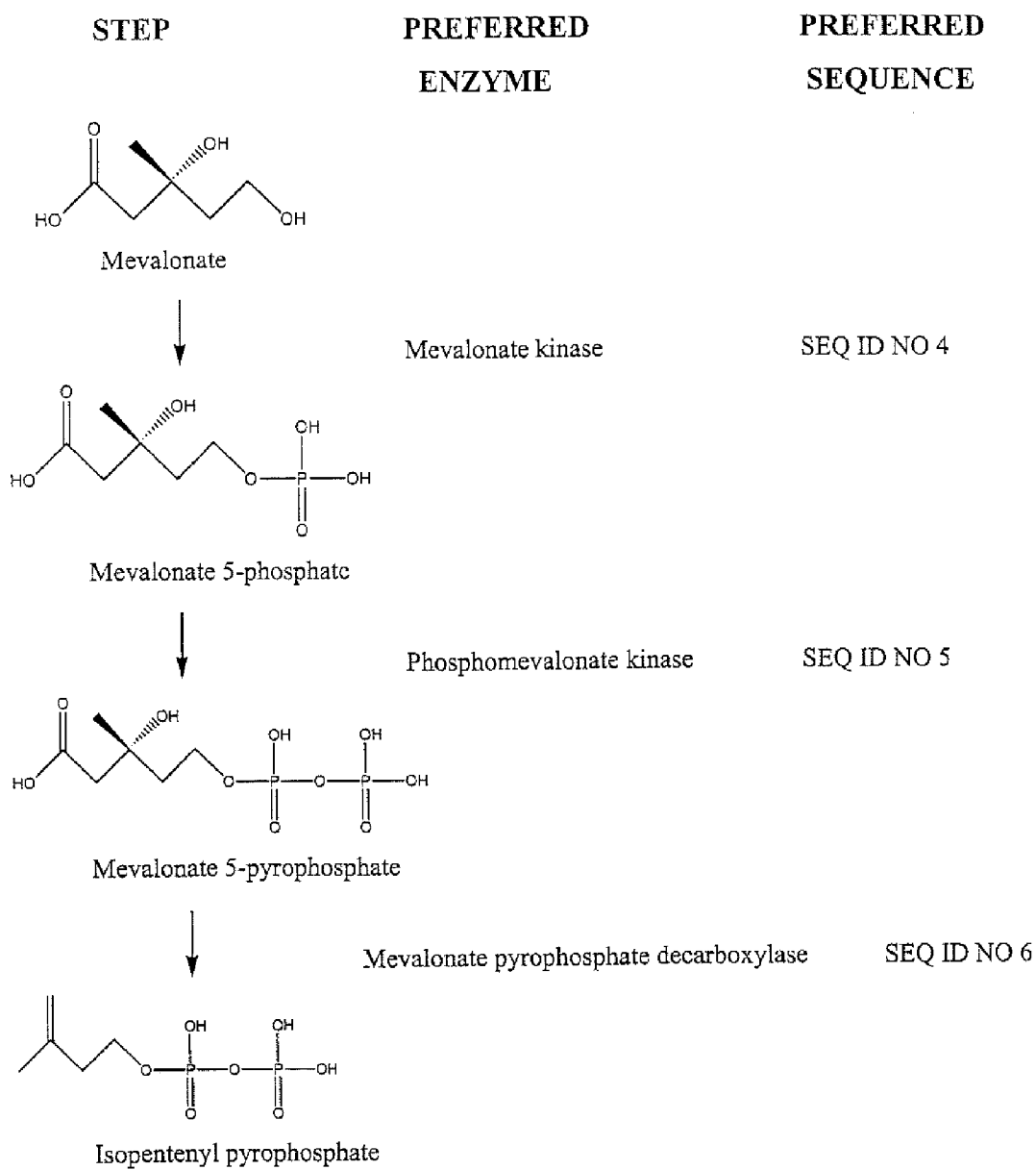

As shown in the schematic of FIGS. 1A and 1B, the mevalonate pathway comprises six steps and involves six intermediates. Initially, two molecules of acetyl-coenzyme A (more commonly referred to as "acetyl-CoA") are combined. Acetyl-CoA is produced naturally by the host microorganism when it is in the presence of a suitable carbon source. For example, eukaryotic cells naturally synthesize acetyl-CoA from compounds derived from sugars and fats. An enzyme capable of condensing two molecules of acetyl-CoA to acetoacetyl-CoA is used in this first step of synthesizing isopentenyl pyrophosphate via the mevalonate pathway.

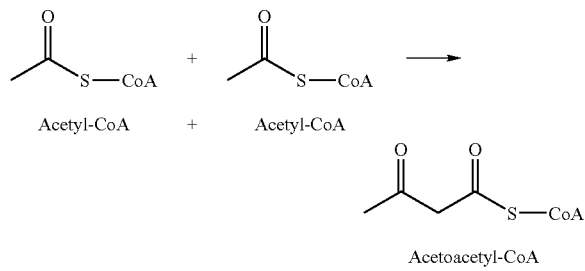

Thus, any DNA fragment coding for an enzyme capable of carrying out this step may be used in the present method. Preferably, however, the DNA fragment codes for an acetoacetyl-CoA thiolase. Genes for such thiolases are known to those of ordinary skill in the art and include, for example, the genes of acetyl-CoA thiolase from *Ralstonia eutrophus* (Peoples et al. (1989), "Poly-β-Hydroxybutyrate Biosynthesis in *Alcaligenes eutrophus* H16" and "Characterization of the Genes Encoding β-Ketothiolase and Acetoacetyl-CoA Reductase," *J. Biol. Chem.* 264 (26): 5293-15297); *Saccharomyces cerevisiae* (*S. cerevisiae*) (Hiser et al. (1994), "ERG10 From *Saccharomyces cerevisiae* Encodes Acetoacetyl-CoA Thiolase," *J. Biol. Chem.* 269 (50): 31383-31389); and *Escherichia coli*. It is particularly preferred, however, that the thiolase encoded by the nucleotide sequence of SEQ ID NO 1 be used in the present method.

The next step in the mevalonate pathway requires the condensation of acetoacetyl-CoA, formed from the preceding step, with yet another molecule of acetyl-CoA to form 3-hydroxy-3-methylglutaryl-CoA (HMG-CoA). This step is catalyzed enzymatically using an enzyme that will condense acetoacetyl-CoA with acetyl-CoA.

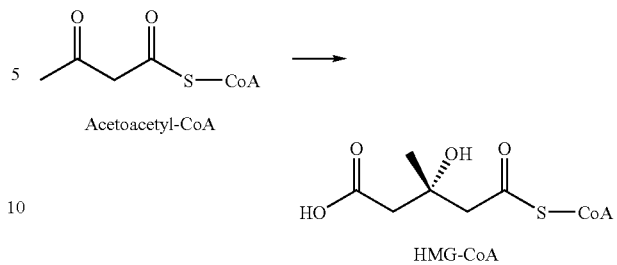

Although any DNA fragment that codes for an enzyme capable of carrying out this step may be used, it is preferred that the DNA fragment code for an HMG-CoA synthase. Known genes for HMG-CoA synthases include, without limitation, the synthases from *Blattella germanica* (Martinez-Gonzalez et al. (1993), "3-Hydroxy-3-Methylglutaryl-Coenzyme-A Synthase from *Blattella germanica*. Cloning, Expression, Developmental Pattern and Tissue Expression," *Eur. J. Biochem.* 217(2), 691-699); and *S. cerevisiae*, and thus, are preferred. A particularly preferred synthase is encoded by the nucleotide sequence of SEQ ID NO 2.

The third step converts HMG-CoA to mevalonate. As with the other steps, this conversion is enzymatically controlled.

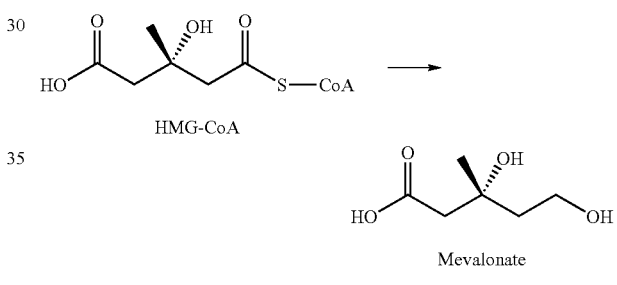

According to the present method, a DNA fragment coding for an enzyme that is capable of converting HMG-CoA into mevalonate is included in the expression vector. The HMG-CoA reductase genes from *Sulfolobus solfataricus* (Bochar (1997), "3-Hydroxy-3-Methylglutaryl-Coenzyme A Reductase of *Sulfolobus solfataricus*: DNA Sequence, Phylogeny, Expression in *Escherichia coli* of the hmgA Gene, and Purification and Kinetic Characterization of the Gene Product," *J. Bacteriol.* 179(11): 3632-3638); *Haloferax volcanii* (Bischoff et al. (1996), "3-Hydroxy-3-Methylglutaryl-Coenzyme A Reductase from *Haloferax volcanii*: Purification, Characterization, and Expression in *Escherichia coli*," *J. Bacteriol.* 178(1):19-23); and *S. cerevisiae* (Basson et al. (1988), "Structural and Functional Conservation Between Yeast and Human 3-Hydroxy-3-Methylglutaryl Coenzyme A Reductases, the Rate-Limiting Enzyme of Sterol Biosynthesis," *Mol Cell Biol.* 8(9): 3797-808) are known, and are consequently preferred for the present methods. It is particularly preferred, however, that the nucleotide sequence of SEQ ID NO 3 that encodes an HMG-CoA reductase be used in the present methods.

The nucleotide sequence defined by SEQ ID NO.3 that encodes an HMG-CoA reductase is a truncated version of the *S. cerevisiae* gene coding for HMG-CoA reductase, HMG1. The protein coded for by HMG1 is an integral membrane protein located in the endoplasmic reticulum of *S. cerevisiae*;

it consists of a membrane-spanning, regulatory domain in its N-terminal region (amino acids 1-552) and a catalytically active domain in its C-terminal region. (See Polakowski (1998), "Overexpression of a Cytosolic Hydroxymethylglutaryl-CoA Reductase Leads to Squalene Accumulation in Yeast," *Appl. Microbiol Biotechnol.* 49:66-71.) The nucleotide sequence defined by SEQ ID NO 3 comprises an artificial start codon, followed by nucleotides 1660-3165 of the HMG1 sequence. Therefore, the nucleotide sequence defined by SEQ ID NO 3 codes for only the catalytically active portion of *S. cervisiae* HMG-CoA reductase.

The fourth step in the mevalonate pathway involves the enzymatic phosphorylation of mevalonate to form mevalonate 5-phosphate.

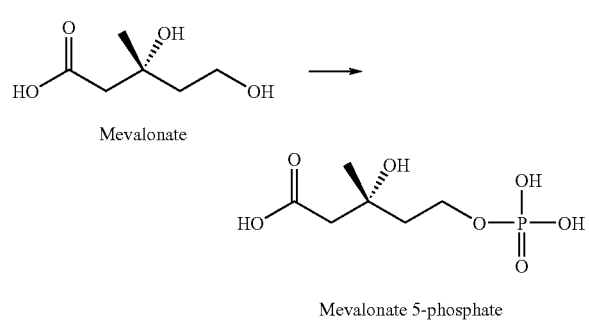

Although any DNA fragment coding for an enzyme capable of mevalonate phosphorylation may be used, it is preferred that a DNA fragment coding specifically for mevalonate kinase be used. Genes for such kinases are known to those of ordinary skill in the art and include, for example, the mevalonate kinase of *S. cerevisiae* (Oulmouden et al. (1991), "Nucleotide Sequence of the ERG12 Gene of *Saccharomyces cerevisiae* Encoding Mevalonate Kinase," Curr. Genet. 19(1): 9-14). A particularly preferred sequence that codes for this particular kinase is identified in SEQ ID NO 4.

The fifth step in the mevalonate pathway requires the addition of a second phosphate group to mevalonate 5-phosphate. An enzyme catalyzes this step.

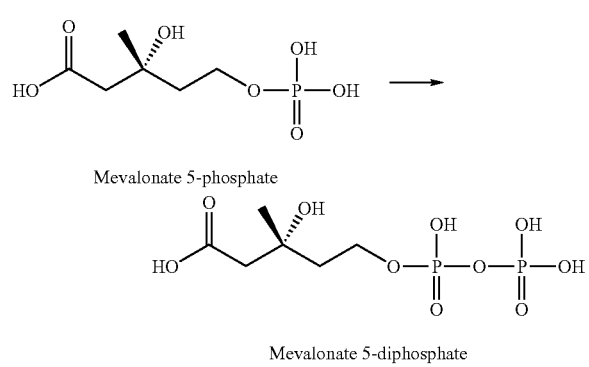

In the present method, a DNA fragment that codes for an enzyme capable of adding a second phosphate group to mevalonate 5-phosphate is used in the expression vector. Preferably, the DNA fragment codes for a phosphomevalonate kinase, such as the gene of the same name obtained from *S. cerevisiae* (Tsay et al. (1991), "Cloning and Characterization of ERG8, an Essential Gene of *Saccharomyces cerevisiae* that Encodes Phosphomevalonate Kinase," *Mol. Cell Biol.* 11(2): 620-31). Such kinases are known to those of ordinary skill in the art and include, for example, the kinase coded by the nucleotide sequence of SEQ ID NO 5.

The sixth and final step of the mevalonate pathway is the enzymatic conversion of mevalonate 5-pyrophosphate into isopentenyl pyrophosphate.

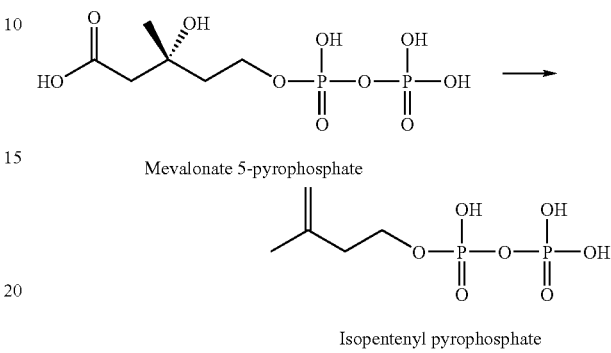

Although any DNA fragment coding for a mevalonate pyrophosphate decarboxylase may be used, it is particularly preferred that the gene from *S. cerevisiae* (Toth et al. (1996), "Molecular Cloning and Expression of the cDNAs Encoding Human and Yeast Mevalonate Pyrophosphate Decarboxylase," *J. Biol. Chem.* 271(14):7895-7898) be used. A particularly preferred DNA fragment is the nucleotide sequence of SEQ ID NO 6.

When an intermediate is introduced, the method additionally requires introduction of DNA fragments that code for enzymes responsible for catalyzing those steps of the mevalonate pathway located "downstream" from the introduced intermediate. With reference to the mevalonate pathway described above and to the biosynthetic schemes provided in FIGS. 1A and 1B, one of ordinary skill in the art can readily determine which DNA fragments and enzymatic steps are necessary when a given intermediate is introduced into the host microorganism.

The mevalonate pathway is contrasted with the mevalonate-independent (or deoxyxylulose-5-phosphate) pathway. In some organisms, isopentenyl pyrophosphate production proceeds by condensation of pyruvate and glyceraldehyde-3-phosphate, via 1-deoxyxylulose-5-phosphate (DXP) as an intermediate. (See Rohmer et al. (1993) *Biochem. J* 295:517-524.) While some organisms have genes for only one pathway, other organisms have genes for both pathways. For a discussion of both the mevalonate and deoxyxylulose 5-phosphate pathways, reference is made to Lange et al. (2000), "Isoprenoid Biosynthesis: The Evolution of Two Ancient and Distinct Pathways Across Genomes," *Proc. Natl. Acad. Sci. USA* 97(24):13172-13177.

Any prokaryotic or eukaryotic host microorganism may be used in the present method so long as it remains viable after being transformed with a sequence of nucleic acids. Generally, although not necessarily, the host microorganism is bacterial. Examples of bacterial host microorganisms include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla,* and *Paracoccus* taxonomical classes. Preferably, the host microorganism is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host microorganism's own metabolic processes and those processes involved with the mevalonate pathway.

Those of ordinary skill in the art can readily identify suitable host microorganisms. For example, cross-talk is minimized or eliminated entirely when the host microorganism relies exclusively on the "deoxyxylulose 5-phosphate" (or "DXP") pathway for synthesizing isopentenyl pyrophosphate. In such host microorganisms, the mevalonate pathway does not inherently influence (save for the additional synthesis of isopentenyl pyrophosphate) the host microorganism, since it lacks any genes that are equipped to process the proteins (i.e., enzymes) or intermediates associated with the mevalonate pathway. Such organisms relying exclusively or predominately on the deoxyxylulose 5-phosphate pathway include, for example, *Escherichia coli*. Of course, it will be recognized by those of ordinary skill in the art that the host microorganism used in the method may also conduct isopentenyl pyrophosphate synthesis via the mevalonate pathway, either exclusively or in combination with the deoxyxylulose 5-phosphate pathway.

Sequences of nucleic acids coding for the desired enzymes of the mevalonate pathway are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in D. M. Matteuci et al. (1980) *Tet. Lett.* 521:719; Caruthers et al. U.S. Pat. No. 4,500,707; and U.S. Pat. Nos. 5,436,327 and 5,700,637 to Southern et al.). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions. (See, for example, U.S. Pat. No. 4,683,195 to Mullis.)

Once each of the individual nucleic acid sequences necessary for carrying out the desired steps of the mevalonate pathway has been determined, each sequence must be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art. (See, for example, U.S. Pat. No. 4,683,195 to Minshull et al.)

For example, each of the desired nucleic acid sequences can be initially generated in a separate polymerase chain reaction (PCR). Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *Escherchia coli*. See Shine et al. (1975) *Nature* 254:34 and Steitz, in *Biological Regulation and Development: Gene Expression* (ed. R. F. Goldberger), vol. 1, p. 349, 1979, Plenum Publishing, N.Y., for discussions of ribosome binding sites in *Escherichia coli*.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example includes the tac promoter. (See deBoer et al. (1983) *Proc. Natl. Acad. Sci. U.S.A.* 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M 13 phage and λ phage; as well as mutant phages, such as λgt-λβ. Of course, such expression vectors may only be suitable for a particular host microorganism. One of ordinary skill in the art, however, can readily determine through routine experimentation whether any particular expression vector is suited for any given host microorganism. For example, the expression vector can be introduced into the host organism, which is then monitored for viability and expression of the sequences contained in the vector. In addition, reference may be made to the relevant texts and literature, which describe expression vectors and their suitability to any particular host microorganism.

The expression vectors of the invention must be introduced or transferred into the host microorganism. Such methods for transferring the expression vectors into host microorganisms are well known to those of ordinary skill in the art. For example, one method for transforming *Escherchia coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host microorganism with a desired sequence using these or other methods.

For identifying a transfected host microorganism, a variety of methods are available. For example, a culture of potentially transfected host microorganisms may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host microorganism is transformed with at least one expression vector. When only a single expression vector is used (without the addition of an intermediate), the vector will contain all of the nucleic acid sequences necessary for carrying out isopentenyl pyrophosphate synthesis via the mevalonate pathway. Although such an all-encompassing expression vector may be used when an intermediate is introduced, only those nucleic acid sequence(s) necessary for converting the intermediate to isopentenyl pyrophosphate are required.

When two versions of an expression vector are used (without the addition of an intermediate), nucleic acid sequences coding for some of the six proteins (i.e., enzymes) necessary for isopentenyl synthesis via the mevalonate pathway may be contained in a first expression vector, while the remainder are contained in a second expression vector. Again, the nucleic acid sequence(s) necessary for converting an introduced intermediate into isopentenyl pyrophosphate will be contained in the expression vector(s). As will be appreciated by those of ordinary skill in the art, a number of different arrangements are possible, and the invention is not limited with respect to the particular arrangement used.

Once the host microorganism has been transformed with the expression vector, the host microorganism is allowed to grow. For microbial hosts, this process entails culturing the cells in a suitable medium. It is important that the culture medium contain an excess carbon source, such as a sugar (e.g., glucose) when an intermediate is not introduced. In this way, cellular production of acetyl-CoA, the starting material necessary for isopentenyl pyrophosphate production in the mevalonate pathway, is ensured. When added, the intermediate is present in an excess amount in the culture medium.

As the host microorganism grows and/or multiplies, expression of the proteins (i.e., enzymes) necessary for carrying out the mevalonate pathway, or for carrying out one or more steps within the pathway, is effected. Once expressed, the enzymes catalyze the steps necessary for carrying out the steps of the mevalonate pathway, i.e., converting acetyl-CoA into isopentenyl pyrophosphate. If an intermediate has been introduced, the expressed enzymes catalyze those steps necessary to convert the intermediate into isopentenyl pyrophosphate. Any means for recovering the isopentenyl pyrophosphate from the host microorganism may be used. For example, the host microorganism may be harvested and subjected to hypotonic conditions, thereby lysing the cells. The lysate may then be centrifuged and the supernatant subjected to high performance liquid chromatography (HPLC). Once the isopentenyl pyrophosphate is recovered, modification may be carried out in the laboratory to synthesize the desired isoprenoid.

If desired, the isopentenyl pyrophosphate may be left in the host microorganism for further processing into the desired isoprenoid in vivo. For example, large amounts of the isoprenoid lycopene are produced in *Escherichia coli* specially engineered with the expression vector pAC-LYC, as shown in Examples 3 and 4. Lycopene can be recovered using any art-known means, such as those discussed above with respect to recovering isopentenyl pyrophosphate. Lycopene is an antioxidant abundant in red tomatoes and may protect males from prostate cancer. (See Stahl et al. (1996) *Ach. Biochem. Biophys.* 336(1):1-9.) Of course, many other isoprenoids can be synthesized through other pathways, and the invention is not limited with respect to the particular "downstream" pathway. Thus, the present method not only provides methods for producing isopentenyl pyrophosphate, but offers methods for producing isoprenoids as well.

Optionally, when it is desired to retain isopentenyl pyrophosphate in the host microorganism for further biochemical processing, it is preferred that the heterologous nucleic acid sequences introduced into the host microorganism also include a DNA fragment coding for an enzyme capable of converting isopentenyl pyrophosphate to dimethylallyl pyrophosphate. As appreciated by those of ordinary skill in the art, a suitable isomerase will catalyze the conversion of isopentenyl pyrophosphate into dimethylallyl pyrophosphate. Such isomerases are known to those of ordinary skill and include, for example, the isopentenyl pyrophosphate isomerase (idi) coded by the nucleotide sequence of SEQ ID NO 10. Isoprenoid biosynthetic pathways require dimethylallyl pyrophosphate, and increased expression of the isomerase ensures that the conversion of isopentenyl diphoshate into dimethylallyl pyrophosphate does not represent a rate-limiting step in the overall pathway.

The present methods thus provide for the biosynthetic production of isopentenyl pyrophosphate and isoprenoids derived therefrom. As stated above, isopentenyl pyrophosphate has been available only in relatively small amounts, and the present methods provide a means for producing relatively large amounts of this important compound.

Further, the invention provides the ability to synthesize increased amounts of isoprenoids. As stated above, isoprenoids represent an important class of compounds and include, for example, food and feed supplements, flavor and odor compounds, and anticancer, antimalarial, antifungal, and antibacterial compounds. Preferred isoprenoids are those selected from the group consisting of monoterpenes, sesquiterpenes, diterpenes, sesterterpenes, triterpenes, tetraterpenes, and steroids. As a class, terpenes are classified based on the number of isoprene units comprised in the compound. Monoterpenes comprise ten carbons or two isoprene units, sesquiterpenes comprise 15 carbons or three isoprene units, diterpenes comprise 20 carbons or four isoprene units, sesterterpenes comprise 25 carbons or five isoprene units, and so forth. Steroids (generally comprising about 27 carbons) are the products of cleaved or rearranged terpenes.

Monoterpenes include, for example, flavors such as limonene, fragrances such as citranellol, and compounds having anticancer activity, such as geraniol. Sesquiterpenes include, without limitation: periplanone B, a cockroach hormone used to lure cockroaches into traps; artemisinin, an antimalarial drug; ginkgolide B, a platelet-activating factor antagonist; forskolin, an inhibitor of adenylate cyclase; and farnesol, a compound shown to have anticancer activity. Non-limiting examples of diterpenes include the antibacterial and antifungal compound casbene and the drug paclitaxel. Among triterpenes ($C_{30}$) and tetraterpenes ($C_{40}$) are carotenoids, which are used as antioxidants, coloring agents in food and cosmetics, and nutritional supplements (e.g., as vitamin A precursors). As pathways to these and other isoprenoids are already known, the invention can advantageously be incorporated into an overall scheme for producing relatively large amounts of a desired isoprenoid.

Conveniently, the invention also provides sequences, enzymes, expression vectors, and host cells or microorganisms for carrying out the present methods. For example, the six genes necessary for isopentenyl pyrophosphate synthesis from acetyl-CoA are conveniently provided in SEQ ID NO 7. In addition, the invention also provides sequences for the first three genes and the last three genes in SEQ ID NOs 8 and 9, respectively. These sequences can easily be included in an expression vector using techniques described herein or other techniques well known to those of ordinary skill in the art. In addition, the invention also provides host cells transformed with one or more of these expression vectors for use in carrying out the present methods.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

Experimental

The practice of the present invention will employ, unless otherwise indicated, conventional techniques of the biosynthetic industry and the like, which are within the skill of the art. Such techniques are explained fully in the literature.

In the following examples, efforts have been made to ensure accuracy with respect to numbers used (e.g., amounts, temperature, etc.), but some experimental error and deviation should be accounted for. Unless indicated otherwise, temperature is in degrees Celsius and pressure is at or near atmospheric pressure at sea level. All reagents, unless otherwise indicated, were obtained commercially.

EXAMPLE 1

Cloning of the Mevalonate Pathway Operons

Assembly of the Mevalonate Operons

Individual genes for a mevalonate-isoprenoid pathway were assembled to form artificial complete and at least one functional operon. Cloning of the nucleic acid sequences coding for the enzymes of the mevalonate pathway was carried out and the reproduced sequences were divided into two operons. In one of the two operons, the last three genes of the biosynthetic pathway (mevalonate kinase (MK)—SEQ ID NO 4; phosphomevalonate kinase, (PMK)—SEQ ID NO 5; and mevalonate pyrophosphate decarboxylase (MPD)—SEQ ID NO 6) were cloned by a polymerase chain reaction (PCR) as one operon by splicing the genes together using overlap extensions (SOEing). This operon is referred to as the mevalonate bottom (MevB) operon (SEQ ID NO 9). In the second of the two operons, the first three genes of the pathway (acetoacetyl-CoA thiolase (atoB)—SEQ ID NO 1; HMG-CoA synthase (HMGS)—SEQ ID NO 2; and a truncated version of HMG-CoA reductase (tHMGR)—SEQ ID NO 3) were cloned as a separate artificial operon using the same technique. This operon is referred to as the mevalonate top (MevT) operon (SEQ ID NO 8). The individual genes were isolated by PCR from genomic DNA of *Saccharomyces cerevisiae* and *Escherichia coli* prepared by established microbiologic protocols. (See Sambrook et al., *Molecular Cloning: a Laboratory Manual*, $3^{rd}$ ed., Cold Harbor Springs Laboratory Press.) The 100 µL PCR reactions contained 1×Pfu buffer, 1.5 mM $MgSO_4$ (Stratagene, La Jolla, Calif.), 200 µM of each dNTP (Gibco BRL™, Life Technologies, Inc., Gaithersburg, Md.), 500 µM of each primer, 100 to 500 ng of template DNA, 5% dimethyl sulfoxide (Sigma, St. Louis, Mo.), and 2.5 U of Pfu Turbo DNA polymerase (Stratagene). The reactions were carried out in a PTC-200 Peltier Thermal Cycler from MJ Research (South San Francisco, Calif.) with the following temperature cycling program: an initial heating step up to 95° C. for four minutes was followed by 30 cycles of 30 seconds of denaturing at 95° C., 30 seconds of annealing at 50° C., and 100 seconds of extension at 72° C., followed by one cycle at 72° C. for ten minutes. Once each gene of the operon was amplified from genomic DNA preparations, the operons were assembled by PCR reactions similar to the procedure described above, but using the amplified DNA of all three genes as template DNA and only the forward primer of the outermost 5' gene and the reverse primer of the outermost 3' gene. The assembled operons were isolated on 0.7% agarose gels and purified using a Qiagen gel purification kit (Valencia, Calif.) according to the manufacturer's instructions.

Cloning Mevalonate Operons into Sequencing and Expression Vectors

As expression of biochemical pathways is often suboptimal from high-copy plasmids containing strong promoters, the artificial mevalonate operon(s) were cloned in a variety of expression vectors to determine the effect of plasmid copy number and promoter strength on expression of the cloned pathway. Prior to testing for pathway expression, the assembled operons were cloned into the pCR4 TOPO vector using the Invitrogen TOPO TA cloning system (Carlsbad, Calif.) for sequencing purposes. Ligation into pCR4 TOPO vector and transformation of *Escherichia coli* TOP10 cells were carried out according to the manufacturer's instructions. The synthetic operons were excised from the sequenced pCR4 TOPO vectors using restriction enzymes and ligated into the high-copy vector pBAD24, which contains the arabinose-inducible araBAD promoter (Guzman et al. (1995) *J. Bacteriology* 177:4121-4130); pTrc99A, which contains the IPTG-inducible tac promoter (Amann et al. (1988) *Gene* 69:301-315); or into pBBR1MCS-3 (Kovach et al. (1995) *Gene* 166:175-176) or pUC19 (Yanisch-Perron et al. (1985) *Gene* 33:103-119), which contain the unregulated Lac promoters (no plasmid-encoded LacI). The MevB operon was digested with PstI and ligated using T4 DNA ligase (New England Biolabs, Inc., Beverly, Mass.) into the PstI site of the low-copy vector, pBBR1MCS-3, containing $P_{Lac}$ promoter and tetracycline resistance marker. The resulting plasmid, which encodes the enzymes responsible for the conversion of mevalonate to isopentenyl pyrophosphate, was named pBBRMevB. The MevT operon was cloned into the SalI site of pBAD24 by digesting with SalI restriction enzyme and ligating with T4 DNA ligase. The resulting plasmid, which encodes the enzymes responsible for the conversion of acetyl-CoA to mevalonate, was named pBADMevT.

Addition of Isopentenyl Pyrophosphate Isomerase to MevB Operon

The syntheses of geranyl pyrophosphate (GPP), farnesyl pyrophosphate (FPP), and geranylgeranyl pyrophosphate (GGPP) require both isopentenyl pyrophosphate (IPP) and its isomer, dimethylallyl pyrophosphate (DMAPP), to create the backbone structure of all isoprenoids. To ensure sufficient production of DMAPP from IPP, an additional gene, idi (encoding isopentenyl pyrophosphate isomerase, SEQ ID NO 10), was amplified by PCR from *Escherichia coli* genomic DNA using primers containing an XmaI restriction enzyme site at the 5' ends. Both the amplified product (containing idi) and pBBRMevB were digested with XmaI and ligated, thereby placing idi at the 3' end of the MevB artificial operon. The resulting operon, containing the MevB operon and idi, is designated MBI (SEQ ID NO 12). The resulting plasmid (containing the operon of genes that encode for enzymes that convert mevalonate to IPP and DMAPP) was named pBBRMBI-2.

Addition of Polyprenyl Pyrophosphate Synthase(s) to MBI Operon

In order to direct products of the mevalonate pathway operons to the different classes of isoprenoids (monoterpenes, sesquiterpenes, diterpenes, etc.), various polyprenyl pyrophosphate synthases were cloned into the MBI operon, such as geranyl diphospsophate (GPP) synthase, farnesyl pyrophosphate (FPP) synthase, and geranylgeranyl pyrophosphate (GGPP) synthase. Polyprenyl pyrophosphate synthases were cloned by PCR using forward primers with a SacII restriction site and reverse primers with a Sac restriction site. Using restriction enzymes and T4 DNA ligase, the polyprenyl pyrophosphate synthases were cloned between the SacII and SacI sites of pBBRMBI-2. For example, farnesyl pyrophosphate synthase gene ispA (SEQ ID NO 11) was isolated by PCR from *Escherichia coli* genomic DNA and cloned between the SacII and SacI sites of pBBRMBI-2, 3' of idi and the MevB operon. The resulting operon, containing the MevB operon, idi, and ispA (SEQ ID NO 11) has been designated MBIS (SEQ ID NO 13). The plasmid, which encodes the enzymes responsible for the synthesis of farnesyl pyrophosphate (FPP) from mevalonate, was named pBBRMBIS-2.

EXAMPLE 2

Functionality of the Engineered Mevalonate Operon(s) by Growth/No-Growth Phenotype Functionality of the various genetic constructs was shown by expression of the artificial mevalonate-isoprenoid pathway. The plasmids were introduced into an *Escherichia coli* host in which the mevalonate-independent (DXP) isoprenoid pathway was inactivated. *Escherichia coli* strain DMY1 (Kuzuyama et al. (1999) *Biosci. Biotechnol. Biochem.* 63:776-778) contains a mutation (insertion/deletion) in the gene encoding for 1-deoxyxylulose 5-phosphate reductoisomerase (or DXR, the second step of the DXP pathway) that causes inactivation of the mevalonate-independent pathway. Since this mutation is lethal to *Escherichila coli*, the strain must be propagated in Luria-Bertoni (LB) medium (available from, for example, Sigma, St. Louis, Mo.) containing 0.5 nM of methylerithrytol (ME), the product of DXR; or it must have an alternate pathway for the production of isopentenyl pyrophosphate.

Cultures of *Escherichia coli* strain DMY1 were made electrocompetent according to the method of Sambrook et al. (above) and transformed with pBBRMBI-2, or both pBBRMBI-2 and pBADMevT. Newly transformed DMY1 cells were first allowed to recover on LB agar plates overnight, and were supplemented with 0.5 mM ME and appropriate antibiotics at 37° C. prior to testing growth on media devoid of ME. DMY1 cells transformed with only pBBRMBI-2 were plated on LB agar devoid of ME, but supplemented with 1 mM DL-mevalonate prepared by incubating 1 volume of 2 M DL-mevalonic acid lactone (Sigma, St. Louis, Mo.) with 1.02 volumes of 2 M KOH at 37° C. for 30 minutes. DMY1 cells transformed with both pBBRMBI-2 and pBADMevT plasmids were plated on LB agar with antibiotics only (no ME or DL-mevalonate). All test plates were incubated for 48 hours at 37° C.

*Escherichia coli* strain DMY1 cells containing pBBMBI-2 were able to grow on LB agar plates with 1 mM DL-mevalonate, whereas *Escherichia coli* DMY1 cells without the plasmid or with pBBR1MCS-3 (empty vector control) did not grow. The MBI operon successfully converted the supplemented mevalonate to isopentenyl pyrophosphate and dimethylallyl pyrophosphate, thereby complementing the dxr deletion.

*Escherichia coli* strain DMY 1 cells containing pBAD-MevT and pBBRMBI-2 were able to grow on LB agar plates not supplemented with DL-mevalonate, whereas *Escherichia Coli* DMY 1 cells without either of the plasmids could not grow on LB agar alone. The expression of the MevT and MBI operons successfully converted acetyl-CoA to isopentenyl pyrophosphate and dimethylallyl pyrophosphate in vivo, thereby restoring growth to *Escherichia coli* strain DMY1, in which the native DXP isoprenoid pathway is inactive.

EXAMPLE 3

Production of Carotenoids from Mevalonate Using the MBI Artificial Operon

The production of a carotenoid was used to demonstrate the benefits of expressing the artificial mevalonate-dependent IPP biosynthetic pathway over the native *Escherichia coli* DXP-isoprenoid pathway. The increased productivity of the mevalonate-dependent isopentenyl pyrophosphate biosynthetic pathway encoded by the synthetic operons was assayed by coupling isopentenyl pyrophosphate production to the production of lycopene. This was accomplished by co-transforming *Escherichia coli* with pAC-LYC, a low-copy broad-host plasmid that expresses the genes encoding the pathway for lycopene production from farnesyl pyrophosphate. The genes expressed from pAC-LYC are crtE (geranylgeranyl pyrophosphate synthase), crtB (phytoene synthase), and crtI (phytoene desaturase) from *Erwinia herbicola*, which were cloned into pACYC184 using methods similar to those described in Examples 1 and 2. *Escherichia coli* naturally produces farnesyl pyrophosphate from two molecules of isopentenyl pyrophosphate and one molecule of dimethylallyl pyrophosphate through the enzyme farnesyl pyrophosphate synthase, ispA (SEQ ID NO 11). Alternatively, more flux can be directed from the mevalonate pathway to the lycopene pathway by including the *Escherichia coli* gene encoding farnesyl pyrophosphate synthase into the artificial operon(s).

From previous experiments (not described herein), it was found that the production of isopentenyl pyrophosphate from the mevalonate pathway operons was greater in the *Escherichia coli* strain DH10B than in the *Escherichia coli* strain DMY1. In order to demonstrate isopentenyl pyrophosphate production from the mevalonate pathway only, the gene encoding 1-deoxyxylulose 5-phosphate reductoisomerase, dxr, was inactivated in *Escherichia coli* strain DH10B by the method detailed by Datsenko et al. (2000.), "One-step Inactivation of Chromosomal Genes in *Escherichia coli* K-12 Using PCR Products," PNAS 97:6640-6645. In the resulting *Escherichia coli* strain, named DPDXR1, the mevalonate independent pathway (or DXP pathway) is inactive, and in order to survive, the strain must either be propagated in LB medium containing 0.5 mM of methylerithrytol (ME) or have an alternate pathway for the production of isopentenyl pyrophosphate.

Figure 2:
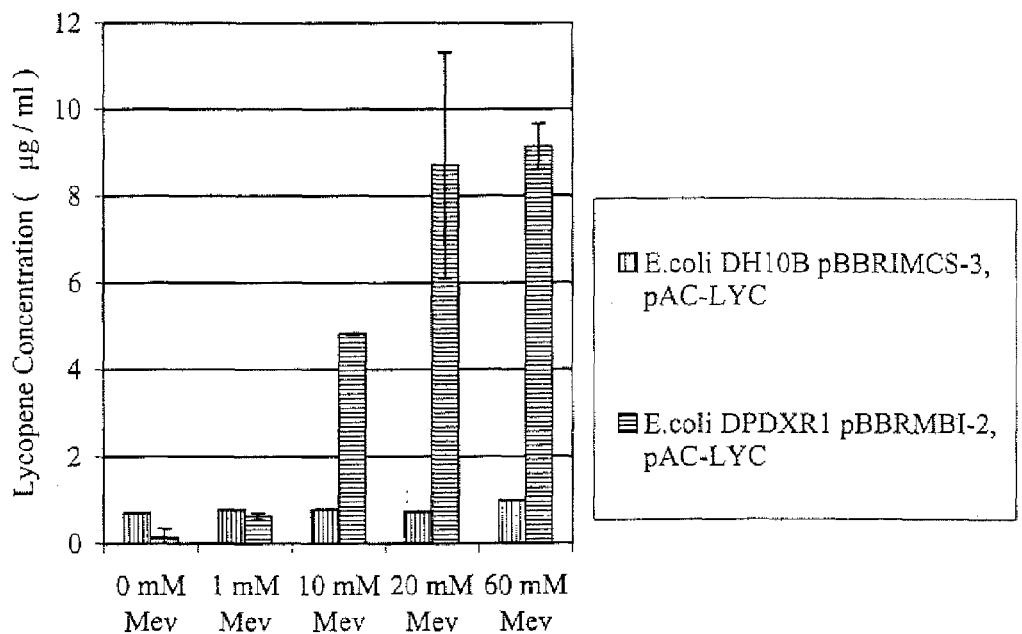
FIG. 2 is a graph illustrating the difference in the concentration of lycopene produced from natural levels of isopentenyl pyrophosphate in non-engineered Escherichia coli and from Escherichia coli engineered to overproduce isopentenyl pyrophosphate from a partial mevalonate-isoprenoid pathway, at different concentrations of mevalonate (Mev).

*Escherichia coli* strain DPDXR1 was transformed with pAC-LYC and pBBRMBI-2, while *Escherichia coli* strain DH10B was transformed with pAC-LYC and pBBR1MCS-3 (control) by electroporation. Transformants were selected on LB agar plates supplemented with 50 µg/ml chloramphenicol, 10 µg/ml tetracycline, and 1 mM DL-mevalonate by incubating overnight at 37° C. One colony of each strain (*Escherichia coli* DPDXR1 harboring pAC-LYC and pBBRMBI-2 or *Escherichia coli* DH10B harboring pAC-LYC and pBBR1MCS-3) was transferred from the LB agar selection plate to 5 ml of LB liquid medium also supplemented with 50 µg/ml chloramphenicol, 10 µg/ml tetracycline, and 1 mM DL-mevalonate. These seed cultures were incubated at 37° C. until they reached a stationary growth phase. The cell density of each seed culture was determined by measuring the optical density of the culture at a wavelength of 600 nm ($OD_{600}$). These seed cultures were then used to inoculate 5 ml test cultures of LB medium with appropriate antibiotics and increasing concentrations of DL-mevalonate. The volume of seed culture used to inoculate each fresh 5 ml culture was calculated to give an initial $OD_{600}$ value of 0.03. Test cultures were incubated for 48 hours at 30° C., after which growth was arrested by chilling the cultures on ice. The optical density of each culture was measured, One ml of each culture was harvested by centrifugation (25000×g, 30 seconds), the supernatant was removed, and cell pellets were suspended in 500 µL of acetone by rapid mixing with a Fisher Vortex Genie 2™ mixer (Scientific Industries, Inc., Bohemia, N.Y.). The acetone/cell mixtures were incubated at 55° C. for 10 minutes to aid in the extraction of lycopene from the cells. Extracted samples were centrifuged (25000×g, 7 minutes) to remove cell debris, and the cleared acetone supernatants were transferred to fresh tubes. The lycopene concentration of each acetone extraction was assayed by absorbance at 470 nm using a Beckman™ DU640 Spectrophotometer (Beckman Coulter, Inc., Fullerton, Calif.) and a 400 µL quartz cuvette. Absorbance values at 470 nm were converted to lycopene concentrations using linear regressions from a standard curve produced using pure lycopene (Sigma, St. Louis, Mo.). Final lycopene concentrations of each strain at increasing concentration of substrate is reported in FIG. 2. As shown in FIG. 2, lycopene production as a function of substrate concentration following shaking for 48 hours at 30° C. demonstrated that lycopene produced from natural levels of isopentenyl pyrophosphate in non-engineered *Escherichia coli* strain DH10B (vertical stripes) remains relatively constant, while lycopene produced from isopentenyl pyrophosphate generated by engineered *Escherichia coli* strain DPDXR1 harboring the plasmid, pBBRMBI-2 (horizontal stripes), significantly increases at mevalonate substrate concentrations of 10 mM and higher.

EXAMPLE 4

Production of Carotenoids from Luria-Bertoni Broth Using the Complete Mevalonate Pathway It was demonstrated that significantly higher levels of isopentenyl pyrophosphate and isoprenoids derived therefrom were produced using the complete mevalonate-isoprenoid operon when compared to the native DXP pathway. The complete mevalonate-isoprenoid pathway was expressed using the two operons, MevT and MBI, which were expressed from pBADMevT and pBBRMBI-2, respectively, and coupled to pAC-LYC to demonstrate the in vivo production of the carotenoid lycopene, using precursors produced by primary cellular metabolism.

Figure 3:
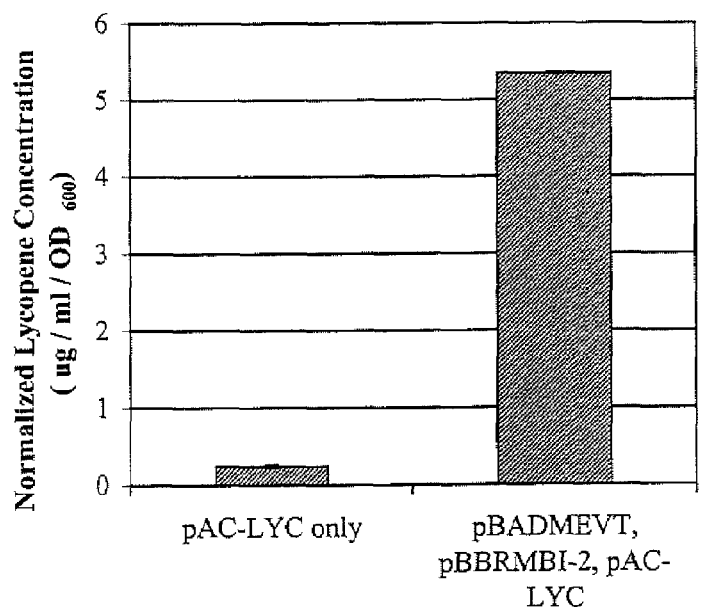
FIG. 3 is a graph illustrating the difference in normalized lycopene concentration produced from natural levels of isopentenyl pyrophosphate in non-engineered Escherichia coli and from Escherichia coli engineered to overproduce isopentenyl pyrophosphate from the complete mevalonate-isoprenoid pathway.

*Escherichia coli* strain DH10B was transformed with pBADMevT, pBBRMBI-2, and pAC-LYC by electroporation. Transformants were selected on LB agar plates containing 50 µg/ml carbenicillin, 10 µg/ml tetracycline, and 50 µg/ml chloramphenicol. A single colony of the strain was transferred from the LB agar plate to 5 ml of LB liquid medium containing the same antibiotics. This seed culture was incubated by shaking at 37° C. until growth reached a stationary phase. The cell density of each seed culture was measured at $OD_{600}$, and the cells were used to inoculate 5 ml test cultures of fresh LB medium plus the same antibiotics to give an $OD_{600}$ of 0.03. The test cultures were incubated for 48 hours at 30° C., after which growth was arrested by chilling the cultures on ice. The remainder of the experimental procedure was followed as described in Example 3. Final lycopene production (µg/ml lycopene per $OD_{600}$) of the pBAD-MevT, pBBRMBI-2, pAC-LYC plasmid system was compared to the lycopene production from pAC-LYC plasmid only (control) in the *Escherichia coli* DH10B strain, as shown in FIG. 3. This figure illustrates, in graph form, the amount of lycopene produced for each strain, normalized for cell density, after shaking for 48 hours at 30° C. The column on the left represents the amount of lycopene produced naturally in a non-engineered *Escherichia coli* strain (containing only pAC-LYC as a control). The column on the right represents the amount of lycopene produced from an *Escherichia coli* strain engineered to overproduce isopentenyl pyrophosphate from the mevalonate-isprenoid pathway.

EXAMPLE 5

Production of Terpenes by Coupling of Artificial Mevalonate Operon(s) to Terpene Cyclases Many valuable natural products were produced from the isoprenoid biosynthetic pathways described herein. Depending on the desired isoprenoid, the described operon(s) were modified, and/or additional operons or other means for chemical synthesis were provided to produce the precursors for the various classes. The following experiments demonstrated the synthesis of sesquiterpenes using the farnesyl pyrophosphate synthase, ispA (SEQ ID NO 11), as well as the means by which other classes of isoprenoids, such as diterpenes, were synthesized by varying the synthase cloned into the operon(s) to create the desired precursor.

In vivo Production of Sesquiterpenes

Amorphadiene, a precursor to the antimalarial drug artemisinin, was produced from the co-expression of the mevalonate-isoprenoid pathway, along with a sesquiterpene cyclase-encoding amorphadiene synthesis. The MBIS operon expressed from pBBRMBIS-2 was coupled with amorpha-4,11-diene synthase (ADS) for the in vivo production of the sesquiterpene amorpha-4,11-diene in *Escherichia coli*.

A gene coding for amorpha-4,11-diene synthase (ADS) was constructed so that, upon translation, the amino acid sequence would be identical to that described by Merke et al. (2000) *Ach. Biochem. Biophys.* 381(2): 173-180. The ADS gene contains recognition sequences 5' and 3' of the coding DNA corresponding to the restriction endonucleases NcoI and XmaI, respectively. The ADS gene was digested to completion with the restriction endonucleases, along with DNA for the plasmid pTrc99A. The 1644-bp gene fragment and the 4155-bp plasmid fragment were purified using 0.7% agarose gels and a Qiagen gel purification kit (Valencia, Calif.) according to the manufacturer's instructions. The two fragments were then ligated using T4 DNA tigase from New England Biolabs (Beverly, Mass.), resulting in plasmid pTRCADS. The insert was verified by sequencing to be the amorpha-4,11-diene synthase gene.

*Escherichia coli* strain DH10B was transformed with both the pBBRMBIS-2 and pTRCADS plasmids by electroporation. Bacterial colonies were then grown on Luria-Bertoni (LB) agar containing 50 µg/ml carbenicillin and 10 µg/ml tetracycline. A single bacterial colony was transferred from the agar plates to 5 ml LB liquid medium containing the same antibiotics and cultured by shaking at 37° C. for 16-18 hours. Five hundred µL of this culture was transferred into 5 ml fresh LB liquid medium with the same antibiotics, then cultured by shaking at 37° C. to an optical density of 0.816 at 600 nm ($OD_{600}$). A 1.6 ml portion of this culture was used to inoculate a flask containing 100 ml of LB liquid medium with 50 µg/ml carbenicillin and 10 µg/ml tetracycline, which was cultured by shaking at 37° C. After 1.5 hours, 1 ml of 1 M mevalonate and 100 µL of 500 mM isopropylthio-β-D-galactoside (IPTG) were added to the culture, and it continued to be shaken at 37° C. Amorpha-4,11-diene concentration was determined by extracting 700 µl samples (taken hourly) with 700 µl of ethyl acetate in glass vials. The samples were then shaken at maximum speed on a Fisher Vortex Genie 2™ mixer (Scientific Industries, Inc., Bohemia, N.Y.) for three minutes. The samples were allowed to settle in order to separate the ethyl acetate-water emulsions. Prior to gas chromatography-mass spectrometry analysis, the ethyl acetate layer was transferred with a glass Pasteur pipette to a clean glass vial.

Ethyl acetate culture extracts were analyzed on a Hewlett-Packard 6890 gas chromatograph/mass spectrometer (GC/MS). A 1 µl sample was separated on the GC using a DB-5 column (available from, for example, Agilent Technologies, Inc., Palo Alto, Calif.) and helium carrier gas. The oven cycle for each sample was 80° C. for two minutes, increasing temperature at 30° C./minute to a temperature of 160° C., increasing temperature at 3° C./min to 170° C., increasing temperature at 50° C./minute to 300° C., and a hold at 300° C. for two minutes. The resolved samples were analyzed by a Hewlett-Packard model 5973 mass selective detector that monitored ions 189 and 204 m/z. Previous mass spectra demonstrated that the amorpha-4,11-diene synthase product was amorphadiene and that amorphadiene had a retention time of 7.9 minutes using this GC protocol. Since pure standards of amorpha-4,11-diene are not available, the concentrations must be quantified in terms of caryophyllene equivalence. A standard curve for caryophyllene has been determined previously, based on a pure standard from Sigma (St. Louis, Mo.). The amorpha-4,11-diene concentration is based on the relative abundance of 189 and 204 m/z ions to the abundance of the total ions in the mass spectra of the two compounds.

Figure 4:
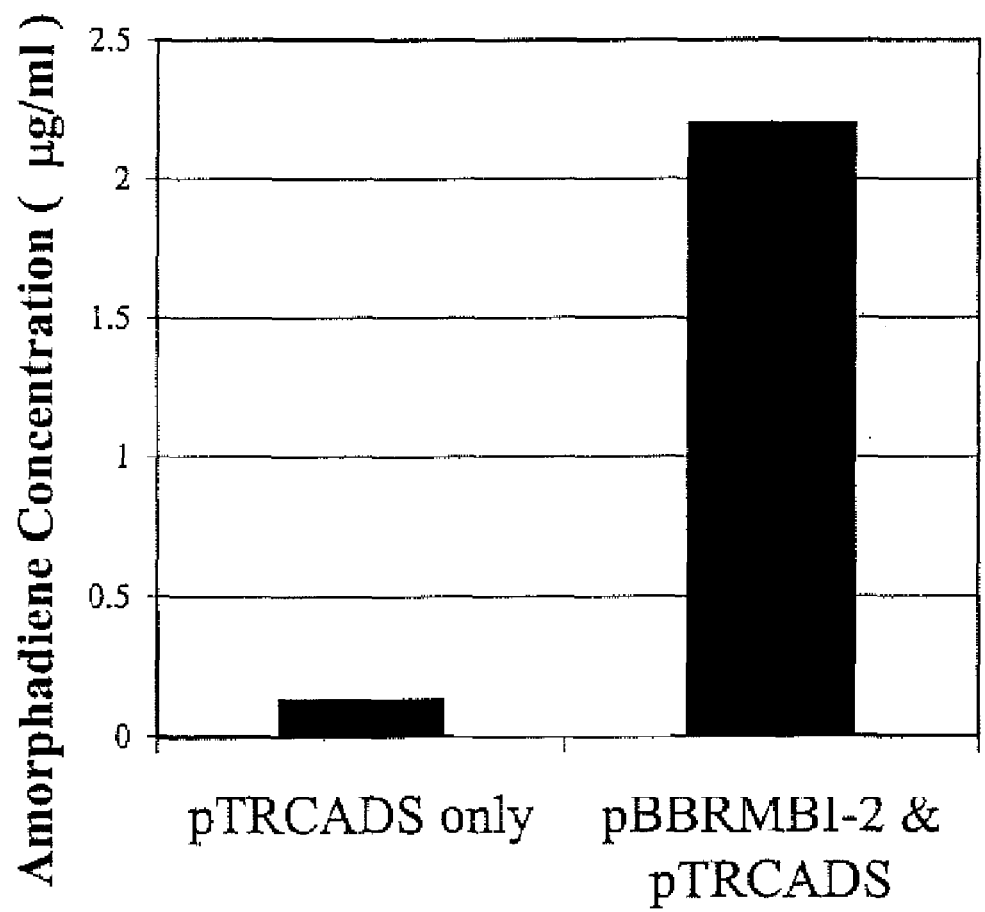
FIG. 4 is a graph illustrating the difference in amorphadiene concentration produced from natural levels of isopentenyl pyrophosphate in non-engineered Escherichia coli and from Escherichia coli engineered to overproduce isopentenyl pyrophosphate from a partial mevatonate-isoprenoid pathway.

The amorphadiene concentration of the cultures seven hours after the addition of IPTG and mevalonate is shown in FIG. 4. The figure shows the concentration of amorphadiene produced seven hours after the addition of mevalonate and isopropylthio-β-D-galactoside (IPTG). The column on the left shows the concentration of amorphadiene produced from non-engineered *Escherichia coli* harboring the pTRCADS plasmid alone. The column on the right shows the concentration of amorphadiene produced from engineered *Escherichia coli* harboring the pBBRMBIS-2 and pTRCADS plasmids. The *Escherichia coli* strain engineered to make farnesyl pyrophosphate from the mevalonate isoprenoid pathway produced 2.2 µg/ml amorphadiene, whereas the non-engineered strain (without the mevalonate isoprenoid pathway) produced only 0.13 µg/ml.

In vivo Production of Diterpenes

The plasmid pBBRMBIS-2 was modified to include a gene encoding geranylgeranyl pyrophosphate synthase (instead of farnesyl pyrophosphate synthase). To demonstrate the utility of the artificial mevalonate-isoprenoid for in vivo diterpene production, this modified expression system was coupled with a plasmid expressing casbene synthase. Casbene synthase CDNA cloned into expression vector pET21-d (Hill et al. (1 996), *Arch Biochem. Biophys.* 336:283-289) was cut out with SalI (New England Biolabs, Beverly, Mass.) and NcoI (New England Biolabs, Beverly, Mass.) and re-cloned into high-copy-number expression vector pTrc99A. The gene fragment and the plasmid fragment were purified with 0.7% agarose gels using a Qiagen gel purification kit (Valencia, Calif.) according to the manufacturer's instructions. The two fragments were then ligated using T4 DNA ligase from New England Biolabs (Beverly, Mass.), resulting in plasmid pTrcCAS.

*Escherichia Coli* strain DH10B was transformed with both the modified pBBRMBIS-2 and pTrcCAS plasmids by electroporation. Bacterial colonies were then grown on Luria-Bertoni (LB) agar containing 50 µg/ml carbenicillin and 10 µg/ml tetracycline. A single bacterial colony was transferred from the agar plates to 5 ml LB liquid medium containing the same antibiotics and cultured by shaking at 37° C. for 16-18 hours. Five hundred microliters of this culture was transferred into 5 ml fresh LB liquid medium with 50 µg/ml carbenicillin and 10 µg/ml tetracycline, and cultured by shaking at 37° C. to an optical density of 0.816 at 600 nm ($OD_{600}$). A 150 µL portion of this culture was used to inoculate a flask containing 25 ml of LB liquid medium with 50 µg/ml carbenicillin, 10 µg/ml tetracycline, and 20 mM mevalonate. This mixture was cultured by shaking at 37° C. After 1.5 hours, 250 µL of 100 mM IPTG were added to the culture, and it continued to be shaken at 37° C. Casbene concentration of the culture was determined hourly by extracting 450 μl samples. To these samples was added 450 μL of ethyl acetate in a glass vial. The samples were then shaken on a Fisher Vortex Genie 2™ mixer (Scientific Industries, Inc., Bohemia, N.Y.) for three minutes. The samples were allowed to settle in order to separate the ethyl acetate-water emulsion. The ethyl acetate layer was transferred with a glass Pasteur pipette to a clean vial.

Figure 5:
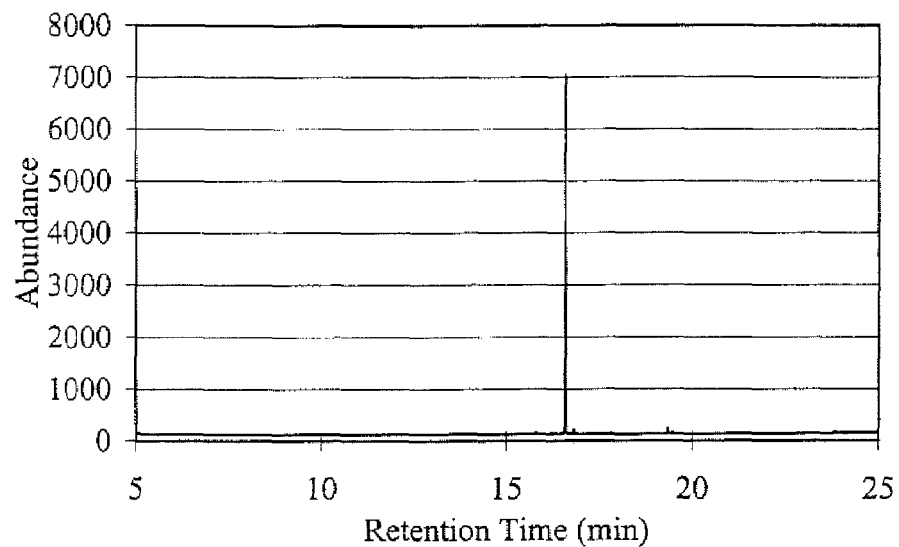
FIG. 5 is a gas chromatographic spectrum illustrating the production of diterpene using ethyl acetate extracts from Escherichia coli engineered to produce isoprenoids from the artificial, modified MBIS operon (a partial mevalonate-isoprenoid pathway), and expressing a casbene cyclase.
Figure 6:
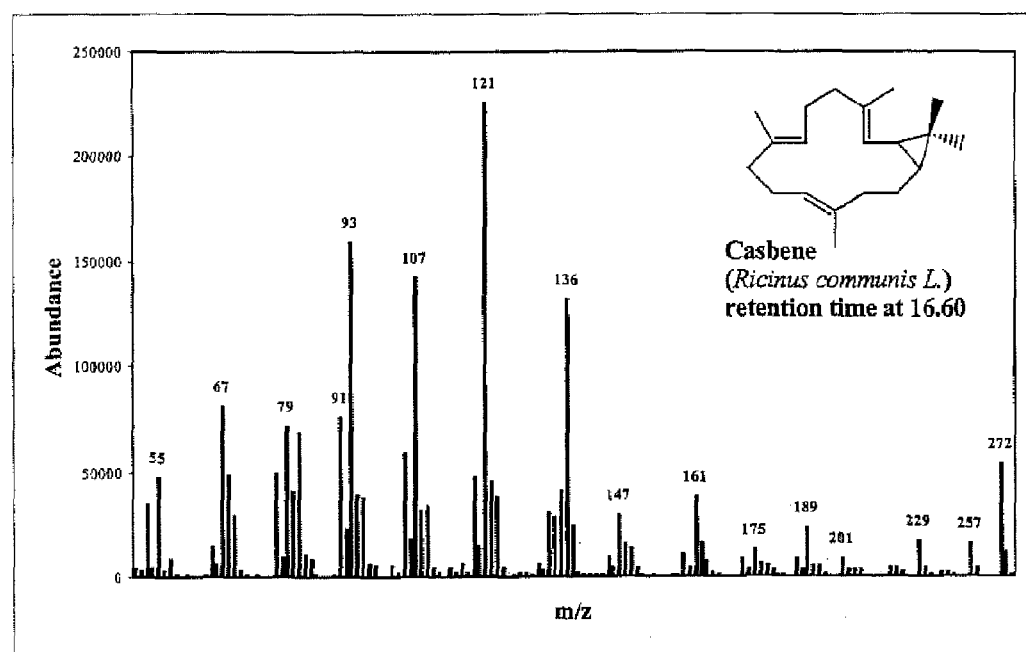
FIG. 6 is the mass spectrum of the isoprenoid casbene.

Ethyl acetate culture extracts were analyzed on a Hewlett-Packard 6890 gas chromatograph/mass spectrometer (GC/MS). A 1 μl sample was separated on the GC using a DB-5 column (available from, for example, Agilent Technologies, Inc., Palo Alto) and helium carrier gas. The oven cycle for each sample was 80° C. for two minutes, increasing temperature at 10° C./minute to a temperature of 300° C., and a hold at 300° C. for two minutes, The resolved samples were analyzed by a Hewlett-Packard model 5973 mass selective detector that monitored ions 229, 257, and 272 m/z. Previous mass spectra had demonstrated that the casbene synthase product was casbene and that casbene had a retention time of 16.6 minutes using this GC protocol. FIG. 5 shows the gas chromatographic analysis and resulting GC/MS chromatogram for the ethyl acetate extracts taken seven hours after addition of IPTG from *Escherichia coli* engineered to produce isoprenoids from the artificial modified MBIS operon, thereby expressing the casbene cyclase from the pTrcCAS plasmid. As a reference, FIG. 6 shows the spectrogram for casbene.

What is claimed is:

1. A method for synthesizing an isoprenoid or an isoprenoid precursor via a mevalonate pathway in a host cell, wherein the method comprises:

i) culturing a transformed host cell in a suitable medium, wherein the medium comprises DL-mevalonate, wherein the transformed host cell is a prokaryote that does not normally synthesize isopentenyl pyrophosphate (IPP) through the mevalonate pathway, and wherein the host cell comprises one or more nucleic acids heterologous to the host cell, wherein the one or more heterologous nucleic acids comprises nucleotide sequences that encode:

(a) a eukaryotic enzyme that phosphorylates mevalonate to mevalonate 5-phosphate;

(b) a eukaryotic enzyme that converts mevalonate 5-phosphate to mevalonate 5-pyrophosphate; and (c) a eukaryotic enzyme that converts mevalonate 5-pyrophosphate to IPP, said culturing providing for production of the enzymes, resulting in synthesis of said isoprenoid or isoprenoid precursor in a recoverable amount of at least about 1 mg/L; and ii) recovering the produced isoprenoid or isoprenoid precursor.

2. The method of claim 1, wherein the one or more heterologous nucleic acids is integrated into the chromosome of the host cell.

3. The method of claim 1, wherein the one or more heterologous nucleic acids is contained in at least one extrachromosomal expression vector.

4. The method of claim 3, wherein the one or more heterologous nucleic acids is present in a single expression vector.

5. The method of claim 1, wherein the nucleotide sequence encoding the enzyme that phosphorylates mevalonate to mevalonate 5-phosphate comprises the nucleotide sequence set forth in SEQ ID NO:4.

6. The method of claim 1, wherein the nucleotide sequence encoding the enzyme that converts mevalonate 5-phosphate to mevalonate 5-pyrophosphate comprises the nucleotide sequence set forth in SEQ ID NO:5.

7. The method of claim 1, wherein the nucleotide sequence encoding the enzyme that converts mevalonate 5-pyrophosphate to IPP comprises the nucleotide sequence set forth in SEQ ID NO:6.

8. The method of claim 1, wherein the heterologous nucleic acid comprises the nucleotide sequence set forth in SEQ ID NO:9.

9. The method of claim 1, wherein the isoprenoid precursor is IPP, and wherein the IPP is further modified enzymatically by the action of isopentenyl pyrophosphate isomerase to provide dimethylallyl pyrophosphate (DMAPP).

10. The method of claim 9, wherein the one or more heterologous nucleic acids further comprises a nucleotide sequence encoding the isopentenyl pyrophosphate isomerase.

11. The method of claim 9, wherein the DMAPP is further modified enzymatic ally with one or more polyprenyl pyrophosphate synthases to provide an isoprenoid.

12. The method of claim 11, wherein the isoprenoid is a monoterpene.

13. The method of claim 12, wherein the monoterpene is selected from limonene, citranellol, and geraniol.

14. The method of claim 11, wherein the isoprenoid is a sesquiterpene.

15. The method of claim 14, wherein the sesquiterpene is selected from periplanone B, artemisinin, ginkgolide B, forskolin, and farnesol.

16. The method of claim 11, wherein the isoprenoid is a diterpene.

17. The method of claim 16, wherein the diterpene is selected from casbene and paclitaxel.

18. The method of claim 11, wherein the isoprenoid is a triterpene.

19. The method of claim 11, wherein the isoprenoid is a tetraterpene.

20. The method of claim 11, wherein the isoprenoid is a steroid.

21. The method of claim 11, wherein the isoprenoid is amorphadiene.

22. The method of claim 11, wherein the isoprenoid is lycopene.

23. The method of claim 1, wherein the prokaryote is *Escherichia coli*.

24. A method for synthesizing an isoprenoid or an isoprenoid precursor via a mevalonate pathway in a host cell, wherein the method comprises:

i) culturing a transformed host cell in a suitable medium, wherein the medium comprises DL-mevalonate, wherein the transformed host cell is a prokaryote that does not normally synthesize isopentenyl pyrophosphate (IPP) through the mevalonate pathway, and wherein the host cell comprises one or more nucleic acids heterologous to the host cell, wherein the one or more heterologous nucleic acids comprises nucleotide sequences that encode:
(a) a eukaryotic enzyme that phosphorylates mevalonate to mevalonate 5-phosphate;
(b) a eukaryotic enzyme that converts mevalonate 5-phosphate to mevalonate 5-pyrophosphate; and
(c) a eukaryotic enzyme that converts mevalonate 5-pyrophosphate to IPP, wherein the host cell is not genetically modified with a heterologous nucleic acid encoding 3-hydroxy-3-methylglutaryl-CoA (HMG-CoA) synthase (HMGS), HMG-CoA reductase, and acetoacetyl-CoA thiolase, said culturing providing for production of the enzymes, resulting in synthesis of said isoprenoid or isoprenoid precursor in a recoverable amount of at least about 1 mg/L; and ii) recovering the produced isoprenoid or isoprenoid precursor.

25. The method of claim 1, wherein the eukaryotic enzyme that phosphorylates mevalonate to mevalonate 5-phosphate, the eukaryotic enzyme that converts mevalonate 5-phosphate to mevalonate 5-pyrophosphate, and the eukaryotic enzyme that converts mevalonate 5-pyrophosphate to IPP are *Saccharomyces cerevisiae* enzymes.

26. A method for synthesizing an isoprenoid or an isoprenoid precursor via a mevalonate pathway in a host cell, wherein the method comprises:

i) culturing a transformed host cell in a suitable medium, wherein the medium comprises DL-mevalonate, wherein the transformed host cell is a prokaryote that does not normally synthesize isopentenyl pyrophosphate (IPP) through the mevalonate pathway, and wherein the host cell comprises one or more nucleic acids heterologous to the host cell, wherein the one or more heterologous nucleic acids comprises the nucleotide sequence set forth in SEQ ID NO:9 that comprises nucleotide sequences encoding:
(a) an enzyme that phosphorylates mevalonate to mevalonate 5-phosphate;
(b) an enzyme that converts mevalonate 5-phosphate to mevalonate 5-pyrophosphate; and
(c) an enzyme that converts mevalonate 5-pyrophosphate to IPP, said culturing providing for production of the enzymes, resulting in synthesis of said isoprenoid or isoprenoid precursor in a recoverable amount of at least about 1 mg/L; and ii) recovering the produced isoprenoid or isoprenoid precursor.

27. The method of claim 26, wherein the isoprenoid precursor is IPP, and wherein the IPP is further modified enzymatically by the action of isopentenyl pyrophosphate isomerase to provide dimethylallyl pyrophosphate (DMAPP).

28. The method of claim 27, wherein the one or more heterologous nucleic acids further comprises a nucleotide sequence encoding the isopentenyl pyrophosphate isomerase.

29. The method of claim 27, wherein the DMAPP is further modified enzymatic ally with one or more polyprenyl pyrophosphate synthases to provide an isoprenoid.

30. The method of claim 29, wherein the isoprenoid is a monoterpene.

31. The method of claim 30, wherein the monoterpene is selected from limonene, citranellol, and geraniol.

32. The method of claim 29, wherein the isoprenoid is a sesquiterpene.

33. The method of claim 32, wherein the sesquiterpene is selected from periplanone B, artemisinin, ginkgolide B, forskolin, and farnesol.

34. The method of claim 29, wherein the isoprenoid is a diterpene.

35. The method of claim 34, wherein the diterpene is selected from casbene and paclitaxel.

36. The method of claim 29, wherein the isoprenoid is a triterpene.

37. The method of claim 29, wherein the isoprenoid is a tetraterpene.

38. The method of claim 29, wherein the isoprenoid is a steroid.

39. The method of claim 29, wherein the isoprenoid is amorphadiene.

40. The method of claim 29, wherein the isoprenoid is lycopene.

41. The method of claim 26, wherein the prokaryote is *Escherichia coli*.

* * * * *

SEQUENCE LISTING

```
<160> NUMBER OF SEQ ID NOS: 13

<210> SEQ ID NO 1
<211> LENGTH: 1185
<212> TYPE: DNA
<213> ORGANISM: Artificial Sequence
<220> FEATURE:
<223> OTHER INFORMATION: Description of Artificial Sequence: Synthetic
      Acetoacetyl-CoA thiolase nucleotide sequence

<400> SEQUENCE: 1
atgaaaaatt gtgtcatcgt cagtgcggta cgtactgcta tcggtagttt taacggttca      60
ctcgcttcca ccagcgccat cgacctgggg gcgacagtaa ttaaagccgc cattgaacgt     120
gcaaaaatcg attcacaaca cgttgatgaa gtgattatgg gtaacgtgtt acaagccggg     180
ctggggcaaa atccggcgcg tcaggcactg ttaaaaagcg ggctggcaga aacggtgtgc     240
ggattcacgg tcaataaagt atgtggttcg ggtcttaaaa gtgtggcgct tgccgcccag     300
gccattcagg caggtcaggc gcagagcatt gtggcgggg gtatggaaaa tatgagttta     360
gccccctact tactcgatgc aaaagcacgc tctggttatc gtcttggaga cggacaggtt     420
tatgacgtaa tcctgcgcga tggcctgatg tgcgccaccc atggttatca tatggggatt     480
accgccgaaa acgtggctaa agagtacgga attacccgtg aaatgcagga tgaactggcg     540
ctacattcac agcgtaaagc ggcagccgca attgagtccg gtgcttttac agccgaaatc     600
gtcccggtaa atgttgtcac tcgaaagaaa accttcgtct tcagtcaaga cgaattcccg     660
aaagcgaatt caacggctga agcgttaggt gcattgcgcc cggccttcga taaagcagga     720
acagtcaccg ctgggaacgc gtctggtatt aacgacggtg ctgccgctct ggtgattatg     780
gaagaatctg cggcgctggc agcaggcctt acccccctgg ctcgcattaa aagttatgcc     840
agcggtggcg tgcccccgc attgatgggt atggggccag tacctgccac gcaaaaagcg     900
ttacaactgg cggggctgca actggcggat attgatctca ttgaggctaa tgaagcattt     960
gctgcacagt tccttgccgt tgggaaaaac ctgggctttg attctgagaa agtgaatgtc    1020
aacggcgggg ccatcgcgct cgggcatcct atcggtgcca gtggtgctcg tattctggtc    1080
acactattac atgccatgca ggcacgcgat aaaacgctgg ggctggcaac actgtgcatt    1140
ggcggcggtc agggaattgc gatggtgatt gaacggttga attaa                    1185

<210> SEQ ID NO 2
<211> LENGTH: 1476
<212> TYPE: DNA
<213> ORGANISM: Artificial Sequence
<220> FEATURE:
<223> OTHER INFORMATION: Description of Artificial Sequence: Synthetic
```

HMG-CoA synthase nucleotide sequence

<400> SEQUENCE: 2

| | | | | | |
|---|---|---|---|---|---|
| atgaaactct | caactaaact | ttgttggtgt | ggtattaaag | gaagacttag | gccgcaaaag | 60 |
| caacaacaat | tacacaatac | aaacttgcaa | atgactgaac | taaaaaaaca | aaagaccgct | 120 |
| gaacaaaaaa | ccagacctca | aaatgtcggt | attaaaggta | tccaaattta | catcccaact | 180 |
| caatgtgtca | accaatctga | gctagagaaa | tttgatggcg | tttctcaagg | taaatacaca | 240 |
| attggtctgg | gccaaaccaa | catgtctttt | gtcaatgaca | gagaagatat | ctactcgatg | 300 |
| tccctaactg | ttttgtctaa | gttgatcaag | agttacaaca | tcgacaccaa | caaaattggt | 360 |
| agattagaag | tcggtactga | aactctgatt | gacaagtcca | agtctgtcaa | gtctgtcttg | 420 |
| atgcaattgt | ttggtgaaaa | cactgacgtc | gaaggtattg | acacgcttaa | tgcctgttac | 480 |
| ggtggtacca | acgcgttgtt | caactctttg | aactggattg | aatctaacgc | atgggatggt | 540 |
| agagacgcca | ttgtagtttg | cggtgatatt | gccatctacg | ataagggtgc | cgcaagacca | 600 |
| accggtggtg | ccggtactgt | tgctatgtgg | atcggtcctg | atgctccaat | tgtatttgac | 660 |
| tctgtaagag | cttcttacat | ggaacacgcc | tacgattttt | acaagccaga | tttcaccagc | 720 |
| gaatatcctt | acgtcgatgg | tcattttca | ttaacttgtt | acgtcaaggc | tcttgatcaa | 780 |
| gtttacaaga | gttattccaa | gaaggctatt | tctaaagggt | tggttagcga | tcccgctggt | 840 |
| tcggatgctt | tgaacgtttt | gaaatatttc | gactacaacg | ttttccatgt | tccaacctgt | 900 |
| aaattggtca | aaatcata | cggtagatta | ctatataacg | atttcagagc | caatcctcaa | 960 |
| ttgttcccag | aagttgacgc | cgaattagct | actcgcgatt | atgacgaatc | tttaaccgat | 1020 |
| aagaacattg | aaaaaacttt | tgttaatgtt | gctaagccat | tccacaaaga | gagagttgcc | 1080 |
| caatctttga | ttgttccaac | aaaacacaggt | aacatgtaca | ccgcatctgt | ttatgccgcc | 1140 |
| tttgcatctc | tattaaacta | tgttggatct | gacgacttac | aaggcaagcg | tgttggttta | 1200 |
| ttttcttacg | gttccggttt | agctgcatct | ctatattctt | gcaaaattgt | tggtgacgtc | 1260 |
| caacatatta | tcaaggaatt | agatattact | aacaaattag | ccaagagaat | caccgaaact | 1320 |
| ccaaaggatt | acgaagctgc | catcgaattg | agagaaaatg | cccatttgaa | gaagaacttc | 1380 |
| aaacctcaag | gttccattga | gcatttgcaa | agtggtgttt | actacttgac | caacatcgat | 1440 |
| gacaaattta | gaagatctta | cgatgttaaa | aaataa | | | 1476 |

<210> SEQ ID NO 3
<211> LENGTH: 1509
<212> TYPE: DNA
<213> ORGANISM: Artificial Sequence
<220> FEATURE:
<223> OTHER INFORMATION: Description of Artificial Sequence: Synthetic
    HMG-CoA reductase nucleotide sequence

<400> SEQUENCE: 3

| | | | | | |
|---|---|---|---|---|---|
| atggttttaa | ccaataaaac | agtcatttct | ggatcgaaag | tcaaaagttt | atcatctgcg | 60 |
| caatcgagct | catcaggacc | ttcatcatct | agtgaggaag | atgattcccg | cgatattgaa | 120 |
| agcttggata | agaaaatacg | tcctttagaa | gaattagaag | cattattaag | tagtggaaat | 180 |
| acaaaacaat | tgaagaacaa | agaggtcgct | gccttggtta | ttcacggtaa | gttacctttg | 240 |
| tacgctttgg | agaaaaaatt | aggtgatact | acgagagcgg | ttgcggtacg | taggaaggct | 300 |
| ctttcaattt | tggcagaagc | tcctgtatta | gcatctgatc | gtttaccata | taaaaattat | 360 |
| gactacgacc | gcgtatttgg | cgcttgttgt | gaaaatgtta | taggttacat | gcctttgccc | 420 |

```
gttggtgtta taggcccctt ggttatcgat ggtacatctt atcatatacc aatggcaact      480
acagagggtt gtttggtagc ttctgccatg cgtggctgta aggcaatcaa tgctggcggt      540
ggtgcaacaa ctgttttaac taaggatggt atgacaagag gcccagtagt ccgtttccca      600
actttgaaaa gatctggtgc ctgtaagata tggttagact cagaagaggg acaaaacgca      660
attaaaaaag cttttaactc tacatcaaga tttgcacgtc tgcaacatat tcaaacttgt      720
ctagcaggag atttactctt catgagattt agaacaacta ctggtgacgc aatgggtatg      780
aatatgattt ctaaaggtgt cgaatactca ttaaagcaaa tggtagaaga gtatggctgg      840
gaagatatgg aggttgtctc cgtttctggt aactactgta ccgacaaaaa accagctgcc      900
atcaactgga tcgaaggtcg tggtaagagt gtcgtcgcag aagctactat tcctggtgat      960
gttgtcagaa aagtgttaaa aagtgatgtt tccgcattgg ttgagttgaa cattgctaag     1020
aatttggttg atctgcaat ggctgggtct gttggtggat ttaacgcaca tgcagctaat     1080
ttagtgacag ctgttttctt ggcattagga caagatcctg cacaaaatgt tgaaagttcc     1140
aactgtataa cattgatgaa agaagtggac ggtgatttga aatttccgt atccatgcca     1200 tccatcgaag taggtaccat cggtggtggt actgttctag aaccacaagg tgccatgttg     1260
gacttattag gtgtaagagg cccgcatgct accgctcctg gtaccaacgc acgtcaatta     1320
gcaagaatag ttgcctgtgc cgtcttggca ggtgaattat ccttatgtgc tgccctagca     1380
gccggccatt tggttcaaag tcatatgacc cacaacagga aacctgctga accaacaaaa     1440
cctaacaatt tggacgccac tgatataaat cgtttgaaag atgggtccgt cacctgcatt     1500
aaatcctaa                                                              1509
```

<210> SEQ ID NO 4
<211> LENGTH: 1332
<212> TYPE: DNA
<213> ORGANISM: Artificial Sequence
<220> FEATURE:
<223> OTHER INFORMATION: Description of Artificial Sequence: Synthetic
      Mevalonate kinase nucleotide sequence

<400> SEQUENCE: 4

```
atgtcattac cgttcttaac ttctgcaccg ggaaaggtta ttattttgg tgaacactct        60 gctgtgtaca caagcctgc cgtcgctgct agtgtgtctg cgttgagaac ctacctgcta      120
ataagcgagt catctgcacc agatactatt gaattggact tcccggacat tagctttaat      180
cataagtggt ccatcaatga tttcaatgcc atcaccgagg atcaagtaaa ctcccaaaaa      240
ttggccaagg ctcaacaagc caccgatggc ttgtctcagg aactcgttag tcttttggat      300
ccgttgttag ctcaactatc cgaatccttc cactaccatg cagcgttttg tttcctgtat      360
atgtttgttt gcctatgccc ccatgccaag aatattaagt tttctttaaa gtctacttta      420
cccatcggtg ctgggttggg ctcaagcgcc tctatttctg tatcactggc cttagctatg      480
gcctacttgg gggggttaat aggatctaat gacttggaaa agctgtcaga aaacgataag      540
catatagtga atcaatgggc cttcataggt gaaaagtgta ttcacggtac cccttcagga      600
atagataacg ctgtggccac ttatggtaat gccctgctat ttgaaaaaga ctcacataat      660
ggaacaataa acacaaacaa ttttaagttc ttagatgatt tcccagccat tccaatgatc      720
ctaacctata ctagaattcc aaggtctaca aaagatcttg ttgctcgcgt tcgtgtgttg      780
gtcaccgaga aatttcctga agttatgaag ccaattctag atgccatggg tgaatgtgcc      840
ctacaaggct tagagatcat gactaagtta agtaaatgta aggcaccga tgacgaggct      900
```

-continued

```
gtagaaacta ataatgaact gtatgaacaa ctattggaat tgataagaat aaatcatgga    960
ctgcttgtct caatcggtgt ttctcatcct ggattagaac ttattaaaaa tctgagcgat   1020
gatttgagaa ttggctccac aaaacttacc ggtgctggtg gcggcggttg ctctttgact   1080
ttgttacgaa gagacattac tcaagagcaa attgacagct caaaaagaa attgcaagat    1140 gattttagtt acgagacatt tgaaacagac ttgggtggga ctgctgctg tttgttaagc    1200 gcaaaaaatt tgaataaaga tcttaaaatc aaatccctag tattccaatt atttgaaaat   1260
aaaactacca caaagcaaca aattgacgat ctattattgc caggaaacac gaatttacca   1320
tggacttcat ag                                                       1332
```

<210> SEQ ID NO 5
<211> LENGTH: 1356
<212> TYPE: DNA
<213> ORGANISM: Artificial Sequence
<220> FEATURE:
<223> OTHER INFORMATION: Description of Artificial Sequence: Synthetic Phosphomevalonate kinase nucleotide sequence

<400> SEQUENCE: 5

```
atgtcagagt tgagagcctt cagtgcccca gggaaagcgt tactagctgg tggatattta     60
gttttagata caaaatatga agcatttgta gtcggattat cggcaagaat gcatgctgta    120
gcccatcctt acggttcatt gcaagggtct gataagtttg aagtgcgtgt gaaaagtaaa    180
caatttaaag atggggagtg gctgtaccat ataagtccta aaagtggctt cattcctgtt    240
tcgataggcg gatctaagaa ccctttcatt gaaaaagtta tcgctaacgt atttagctac    300
tttaaaccta acatggacga ctactgcaat agaaacttgt tcgttattga tattttctct    360
gatgatgcct accattctca ggaggatagc gttaccgaac atcgtggcaa cagaagattg    420
agttttcatt cgcacagaat tgaagaagtt cccaaaacag gctgggctc ctcggcaggt    480 ttagtcacag ttttaactac agctttggcc tccttttttg tatcggacct ggaaaataat    540
gtagacaaat atagagaagt tattcataat ttagcacaag ttgctcattg tcaagctcag    600
ggtaaaattg gaagcgggtt tgatgtagcg gcggcagcat atggatctat cagatataga    660
agattcccac ccgcattaat ctctaatttg ccagatattg gaagtgctac ttacggcagt    720
aaactggcgc atttggttga tgaagaagac tggaatatta cgattaaaag taaccattta    780
ccttcgggat taactttatg gatgggcgat attaagaatg gttcagaaac agtaaaactg    840
gtccagaagg taaaaaattg gtatgattcg catatgccag aaagcttgaa atatatacca    900
gaactcgatc atgcaaattc tagatttatg gatggactat ctaaactaga tcgcttacac    960
gagactcatg acgattacag cgatcagata tttgagtctc ttgagaggaa tgactgtacc   1020
tgtcaaaagt atcctgaaat cacagaagtt agagatgcag ttgccacaat tagacgttcc   1080
tttagaaaaa taactaaaga atctggtgcc gatatcgaac ctcccgtaca aactagctta   1140
ttggatgatt gccagacctt aaaaggagtt cttacttgct taatacctgg tgctggtggt   1200
tatgacgcca ttgcagtgat tactaagcaa gatgttgatc ttagggctca aaccgctaat   1260
gacaaaagat tttctaaggt tcaatggctg gatgtaactc aggctgactg gggtgttagg   1320
aaagaaaaag atccggaaac ttatcttgat aaatag                             1356
```

<210> SEQ ID NO 6
<211> LENGTH: 1191
<212> TYPE: DNA
<213> ORGANISM: Artificial Sequence
<220> FEATURE:

<223> OTHER INFORMATION: Description of Artificial Sequence: Synthetic
Mevalonate pyrophosphate decarboxylase nucleotide
sequence

<400> SEQUENCE: 6

```
atgaccgttt acacagcatc cgttaccgca cccgtcaaca tcgcaaccct taagtattgg      60
gggaaaaggg acacgaagtt gaatctgccc accaattcgt ccatatcagt gactttatcg    120
caagatgacc tcagaacgtt gacctctgcg gctactgcac ctgagtttga acgcgacact    180
ttgtggttaa atggagaacc acacagcatc gacaatgaaa gaactcaaaa ttgtctgcgc    240
gacctacgcc aattaagaaa ggaaatggaa tcgaaggacg cctcattgcc acattatct    300
caatggaaac tccacattgt ctccgaaaat aactttccta cagcagctgg tttagcttcc    360
tccgctgctg gctttgctgc attggtctct gcaattgcta agttatacca attaccacag    420
tcaacttcag aaatatctag aatagcaaga aaggggtctg gttcagcttg tagatcgttg    480
tttggcggat acgtggcctg ggaaatggga aaagctgaag atggtcatga ttccatggca    540
gtacaaatcg cagacagctc tgactggcct cagatgaaag cttgtgtcct agttgtcagc    600
gatattaaaa aggatgtgag ttccactcag ggtatgcaat tgaccgtggc aacctccgaa    660
ctatttaaag aaagaattga acatgtcgta ccaaagagat ttgaagtcat gcgtaaagcc    720
attgttgaaa aagatttcgc caccctttgca aggaaacaa tgatggattc caactctttc    780
catgccacat gtttggactc tttccctcca atattctaca tgaatgacac ttccaagcgt    840
atcatcagtt ggtgccacac cattaatcag ttttacggag aaacaatcgt tgcatacacg    900
tttgatgcag gtccaaatgc tgtgttgtac tacttagctg aaaatgagtc gaaactcttt    960
gcatttatct ataaattgtt tggctctgtt cctggatggg acaagaaatt tactactgag   1020
cagcttgagg ctttcaacca tcaatttgaa tcatctaact ttactgcacg tgaattggat   1080
cttgagttgc aaaaggatgt tgccagagtg attttaactc aagtcggttc aggcccacaa   1140
gaaacaaacg aatctttgat tgacgcaaag actggtctac aaaggaata a              1191
```

<210> SEQ ID NO 7
<211> LENGTH: 9253
<212> TYPE: DNA
<213> ORGANISM: Artificial Sequence
<220> FEATURE:
<223> OTHER INFORMATION: Description of Artificial Sequence: Synthetic
"single operon" nucleotide sequence

<400> SEQUENCE: 7

```
gacgcttttt atcgcaactc tctactgttt ctccataccc gttttttttgg gctagcagga      60
ggaattcacc atggtacccg ggaggaggat tactatatgc aaacggaaca cgtcattta    120
ttgaatgcac agggagttcc cacgggtacg ctggaaaagt atgccgcaca cacggcagac    180
acccgcttac atctcgcgtt ctccagttgg ctgtttaatg ccaaaggaca attattagtt    240
acccgccgcg cactgagcaa aaaagcatgg cctggcgtgt ggactaactc ggtttgtggg    300
cacccacaac tgggagaaag caacgaagac gcagtgatcc gccgttgccg ttatgagctt    360
ggcgtggaaa ttacgcctcc tgaatctatc tatcctgact ttcgctaccg cgccaccgat    420
ccgagtggca ttgtgaaaaa tgaagtgtgt ccggtatttg ccgcacgcac cactagtgcg    480
ttacagatca atgatgatga agtgatggat tatcaatggt gtgatttagc agatgtatta    540
cacggtattg atgccacgcc gtgggcgttc agtccgtgga tggtgatgca ggcgacaaat    600
cgcgaagcca gaaaacgatt atctgcattt acccagctta ataacccgg ggatcctcta    660
```

-continued

| | |
|---|---|
| gagtcgacta ggaggaatat aaaatgaaaa attgtgtcat cgtcagtgcg gtacgtactg | 720 |
| ctatcggtag ttttaacggt tcactcgctt ccaccagcgc catcgacctg ggggcgacag | 780 |
| taattaaagc cgccattgaa cgtgcaaaaa tcgattcaca acacgttgat gaagtgatta | 840 |
| tgggtaacgt gttacaagcc gggctggggc aaaatccggc gcgtcaggca ctgttaaaaa | 900 |
| gcgggctggc agaaacggtg tgcggattca cggtcaataa agtatgtggt tcgggtctta | 960 |
| aaagtgtggc gcttgccgcc caggccattc aggcaggtca ggcgcagagc attgtggcgg | 1020 |
| ggggtatgga aaatatgagt ttagccccct acttactcga tgcaaaagca cgctctggtt | 1080 |
| atcgtcttgg agacggacag gtttatgacg taatcctgcg cgatggcctg atgtgcgcca | 1140 |
| cccatggtta tcatatgggg attaccgccg aaaacgtggc taaagagtac ggaattaccc | 1200 |
| gtgaaatgca ggatgaactg gcgctacatt cacagcgtaa agcggcagcc gcaattgagt | 1260 |
| ccggtgcttt tacagccgaa atcgtcccgg taaatgttgt cactcgaaag aaaaccttcg | 1320 |
| tcttcagtca agacgaattc ccgaaagcga attcaacggc tgaagcgtta ggtgcattgc | 1380 |
| gcccggcctt cgataaagca ggaacagtca ccgctgggaa cgcgtctggt attaacgacg | 1440 |
| gtgctgccgc tctggtgatt atggaagaat ctgcggcgct ggcagcaggc cttacccccc | 1500 |
| tggctcgcat taaaagttat gccagcggtg gcgtgccccc cgcattgatg ggtatggggc | 1560 |
| cagtacctgc cacgcaaaaa gcgttacaac tggcggggct gcaactggcg gatattgatc | 1620 |
| tcattgaggc taatgaagca tttgctgcac agttccttgc cgttgggaaa aacctgggct | 1680 |
| ttgattctga gaaagtgaat gtcaacggcg gggccatcgc gctcgggcat cctatcggtg | 1740 |
| ccagtggtgc tcgtattctg gtcacactat tacatgccat gcaggcacgc gataaaacgc | 1800 |
| tggggctggc aacactgtgc attggcgcg gtcagggaat tgcgatggtg attgaacggt | 1860 |
| tgaattaagg aggacagcta atgaaactc tcaactaaac tttgttggtg tggtattaaa | 1920 |
| ggaagactta ggccgcaaaa gcaacaacaa ttacacaata caaacttgca aatgactgaa | 1980 |
| ctaaaaaaac aaaagaccgc tgaacaaaaa accagacctc aaaatgtcgg tattaaaggt | 2040 |
| atccaaattt acatcccaac tcaatgtgtc aaccaatctg agctagagaa atttgatggc | 2100 |
| gtttctcaag gtaaatacac aattggtctg ggccaaacca acatgtcttt tgtcaatgac | 2160 |
| agagaagata tctactcgat gtccctaact gttttgtcta agttgatcaa gagttacaac | 2220 |
| atcgacacca acaaaattgg tagattagaa gtcggtactg aaactctgat tgacaagtcc | 2280 |
| aagtctgtca agtctgtctt gatgcaattg tttggtgaaa acactgacgt cgaaggtatt | 2340 |
| gacacgctta atgcctgtta cggtggtacc aacgcgttgt tcaactcttt gaactggatt | 2400 |
| gaatctaacg catgggatgg tagagacgcc attgtagttt gcggtgatat tgccatctac | 2460 |
| gataagggtg ccgcaagacc aaccggtggt gccggtactg ttgctatgtg gatcggtcct | 2520 |
| gatgctccaa ttgtatttga ctctgtaaga gcttcttaca tggaacacgc ctacgatttt | 2580 |
| tacaagccag atttcaccag cgaatatcct tacgtcgatg gtcattttc attaacttgt | 2640 |
| tacgtcaagg ctcttgatca agtttacaag agttattcca agaaggctat ttctaaaggg | 2700 |
| ttggttagcg atcccgctgg ttcggatgct ttgaacgttt tgaaatattt cgactacaac | 2760 |
| gttttccatg ttccaacctg taaattggtc acaaaatcat acggtagatt actatataac | 2820 |
| gatttcagag ccaatcctca attgttccca gaagttgacg ccgaattagc tactcgcgat | 2880 |
| tatgacgaat cttttaaccga taagaacatt gaaaaaactt tgttaatgt tgctaagcca | 2940 |
| ttccacaaag agagagttgc ccaatctttg attgttccaa caaacacagg taacatgtac | 3000 |
| accgcatctg tttatgccgc ctttgcatct ctattaaact atgttggatc tgacgactta | 3060 |

```
caaggcaagc gtgttggttt attttcttac ggttccggtt tagctgcatc tctatattct    3120
tgcaaaattg ttggtgacgt ccaacatatt atcaaggaat tagatattac taacaaatta    3180
gccaagagaa tcaccgaaac tccaaaggat tacgaagctg ccatcgaatt gagagaaaat    3240
gcccatttga agaagaactt caaacctcaa ggttccattg agcatttgca aagtggtgtt    3300
tactacttga ccaacatcga tgacaaattt agaagatctt acgatgttaa aaataagga    3360
ggattacact atggttttaa ccaataaaac agtcatttct ggatcgaaag tcaaaagttt    3420
atcatctgcg caatcgagct catcaggacc ttcatcatct agtgaggaag atgattcccg    3480
cgatattgaa agcttggata agaaaatacg tcctttagaa gaattagaag cattattaag    3540
tagtggaaat acaaaacaat tgaagaacaa agaggtcgct gccttggtta ttcacggtaa    3600
gttaccttg tacgctttgg agaaaaaatt aggtgatact acgagagcgg ttgcggtacg    3660
taggaaggct cttcaatttt tggcagaagc tcctgtatta gcatctgatc gtttaccata    3720
taaaaattat gactacgacc gcgtatttgg cgcttgttgt gaaaatgtta taggttacat    3780
gcctttgccc gttggtgtta taggccccctt ggttatcgat ggtacatctt atcatatacc    3840
aatggcaact acagagggtt gtttggtagc ttctgccatg cgtggctgta aggcaatcaa    3900
tgctggcggt ggtgcaacaa ctgttttaac taaggatggt atgacaagag gcccagtagt    3960
ccgtttccca actttgaaaa gatctggtgc ctgtaagata tggttagact cagaagaggg    4020
acaaaacgca attaaaaaag cttttaactc tacatcaaga tttgcacgtc tgcaacatat    4080
tcaaacttgt ctagcaggag atttactctt catgagattt agaacaacta ctggtgacgc    4140
aatgggtatg aatatgattt ctaaaggtgt cgaatactca ttaaagcaaa tggtagaaga    4200
gtatggctgg gaagatatgg aggttgtctc cgtttctggt aactactgta ccgacaaaaa    4260
accagctgcc atcaactgga tcgaaggtcg tggtaagagt gtcgtcgcag aagctactat    4320
tcctggtgat gttgtcagaa aagtgttaaa aagtgatgtt ccgcattgg ttgagttgaa    4380
cattgctaag aatttggttg gatctgcaat ggctgggtct gttggtggat taacgcaca    4440
tgcagctaat ttagtgacag ctgttttctt ggcattagga caagatcctg cacaaaatgt    4500
tgaaagttcc aactgtataa cattgatgaa agaagtggac ggtgatttga gaatttccgt    4560
atccatgcca tccatcgaag taggtaccat cggtggtggt actgttctag aaccacaagg    4620
tgccatgttg gacttattag gtgtaagagg cccgcatgct accgctcctg gtaccaacgc    4680
acgtcaatta gcaagaatag ttgcctgtgc cgtcttggca ggtgaattat ccttatgtgc    4740
tgccctagca gccggccatt tggttcaaag tcatatgacc cacaacagga aacctgctga    4800
accaacaaaa cctaacaatt tggacgccac tgatataaat cgtttgaaag atgggtccgt    4860
cacctgcatt aaatcctaag tcgacctgca gtaggaggaa ttaccatgt cattaccgtt    4920
cttaacttct gcaccgggaa aggttattat ttttggtgaa cactctgctg tgtacaacaa    4980
gcctgccgtc gctgctagtg tgtctgcgtt gagaacctac ctgctaataa gcgagtcatc    5040
tgcaccagat actattgaat tggacttccc ggacattagc tttaatcata agtggtccat    5100
caatgatttc aatgccatca ccgaggatca agtaaactcc caaaaattgg ccaaggctca    5160
acaagccacc gatggcttgt ctcaggaact cgttagtctt ttggatccgt tgttagctca    5220
actatccgaa tccttccact accatgcagc gttttgtttc ctgtatatgt tgtttgcct    5280
atgcccccat gccaagaata ttaagttttc tttaaagtct actttaccca tcggtgctgg    5340
gttgggctca agcgcctcta tttctgtatc actggcctta gctatggcct acttgggggg    5400
```

```
gttaatagga tctaatgact tggaaaagct gtcagaaaac gataagcata tagtgaatca   5460
atgggccttc ataggtgaaa agtgtattca cggtacccct tcaggaatag ataacgctgt   5520
ggccacttat ggtaatgccc tgctatttga aaaagactca cataatggaa caataaacac   5580
aaacaatttt aagttcttag atgatttccc agccattcca atgatcctaa cctatactag   5640
aattccaagg tctacaaaag atcttgttgc tcgcgttcgt gtgttggtca ccgagaaatt   5700
tcctgaagtt atgaagccaa ttctagatgc catgggtgaa tgtgccctac aaggcttaga   5760
gatcatgact aagttaagta aatgtaaagg caccgatgac gaggctgtag aaactaataa   5820
tgaactgtat gaacaactat tggaattgat aagaataaat catggactgc ttgtctcaat   5880
cggtgtttct catcctggat tagaacttat taaaaatctg agcgatgatt tgagaattgg   5940
ctccacaaaa cttaccggtg ctggtggcgg cggttgctct ttgactttgt tacgaagaga   6000
cattactcaa gagcaaattg acagcttcaa aaagaaattg caagatgatt ttagttacga   6060
gacatttgaa acagacttgg gtgggactgg ctgctgtttg ttaagcgcaa aaaatttgaa   6120
taaagatctt aaaatcaaat ccctagtatt ccaattattt gaaaataaaa ctaccacaaa   6180
gcaacaaatt gacgatctat tattgccagg aaacacgaat ttaccatgga cttcatagga   6240
ggcagatcaa atgtcagagt tgagagcctt cagtgcccca gggaaagcgt tactagctgg   6300
tggatattta gttttagata caaaatatga agcatttgta gtcggattat cggcaagaat   6360
gcatgctgta gcccatcctt acggttcatt gcaagggtct gataagtttg aagtgcgtgt   6420
gaaaagtaaa caatttaaag atggggagtg gctgtaccat ataagtccta aaagtggctt   6480
cattcctgtt tcgataggcg gatctaagaa ccctttcatt gaaaaagtta tcgctaacgt   6540
atttagctac tttaaaccta acatggacga ctactgcaat agaaacttgt tcgttattga   6600
tattttctct gatgatgcct accattctca ggaggatagc gttaccgaac atcgtggcaa   6660
cagaagattg agttttcatt cgcacagaat tgaagaagtt cccaaaacag ggctgggctc   6720
ctcggcaggt ttagtcacag ttttaactac agctttggcc tccttttttg tatcggacct   6780
ggaaaataat gtagacaaat atagagaagt tattcataat ttagcacaag ttgctcattg   6840
tcaagctcag ggtaaaattg aagcgggtt tgatgtagcg gcggcagcat atggatctat   6900
cagatataga agattcccac ccgcattaat ctctaatttg ccagatattg gaagtgctac   6960
ttacggcagt aaactggcgc atttggttga tgaagaagac tggaatatta cgattaaaag   7020
taaccattta ccttcgggat taactttatg gatgggcgat attaagaatg gttcagaaac   7080
agtaaaactg gtccagaagg taaaaaattg gtatgattcg catatgccag aaagcttgaa   7140
aatatataca gaactcgatc atgcaaattc tagatttatg gatggactat ctaaactaga   7200
tcgcttacac gagactcatg acgattacag cgatcagata tttgagtctc ttgagaggaa   7260
tgactgtacc tgtcaaaagt atcctgaaat cacagaagtt agagatgcag ttgccacaat   7320
tagacgttcc tttagaaaaa taactaaaga atctggtgcc gatatcgaac ctcccgtaca   7380
aactagctta ttggatgatt gccagaccct aaaaggagtt cttacttgct taatacctgg   7440
tgctggtggt tatgacgcca ttgcagtgat tactaagcaa gatgttgatc ttagggctca   7500
aaccgctaat gacaaaagat tttctaaggt tcaatggctg gatgtaactc aggctgactg   7560
gggtgttagg aaagaaaaag atccggaaac ttatcttgat aaataggagg taatactcat   7620
gaccgtttac acagcatccg ttaccgcacc cgtcaacatc gcaacccctta agtattgggg   7680
gaaaagggac acgaagttga atctgcccac caattcgtcc atatcagtga ctttatcgca   7740
agatgacctc agaacgttga cctctgcggc tactgcacct gagtttgaac gcgacacttt   7800
```

-continued

```
gtggttaaat ggagaaccac acagcatcga caatgaaaga actcaaaatt gtctgcgcga       7860
cctacgccaa ttaagaaagg aaatggaatc gaaggacgcc tcattgccca cattatctca       7920
atggaaactc cacattgtct ccgaaaataa ctttcctaca gcagctggtt tagcttcctc       7980
cgctgctggc tttgctgcat tggtctctgc aattgctaag ttataccaat taccacagtc       8040
aacttcagaa atatctagaa tagcaagaaa ggggtctggt tcagcttgta gatcgttgtt       8100
tggcggatac gtggcctggg aaatgggaaa agctgaagat ggtcatgatt ccatggcagt       8160
acaaatcgca gacagctctg actggcctca gatgaaagct tgtgtcctag ttgtcagcga       8220
tattaaaaag gatgtgagtt ccactcaggg tatgcaattg accgtggcaa cctccgaact       8280
atttaaagaa agaattgaac atgtcgtacc aaagagattt gaagtcatgc gtaaagccat       8340
tgttgaaaaa gatttcgcca cctttgcaaa ggaaacaatg atggattcca actctttcca       8400
tgccacatgt ttggactctt tccctccaat attctacatg aatgacactt ccaagcgtat       8460
catcagttgg tgccacacca ttaatcagtt ttacggagaa acaatcgttg catacacgtt       8520
tgatgcaggt ccaaatgctg tgttgtacta cttagctgaa aatgagtcga aactcttttgc       8580 atttatctat aaattgtttg gctctgttcc tggatgggac aagaaattta ctactgagca       8640
gcttgaggct ttcaaccatc aatttgaatc atctaacttt actgcacgtg aattggatct       8700
tgagttgcaa aaggatgttg ccagagtgat tttaactcaa gtcggttcag gcccacaaga       8760
aacaaacgaa tctttgattg acgcaaagac tggtctacca aaggaataac tgcaggcatg       8820
caagcttggc tgttttggcg gatgagagaa gattttcagc ctgatacaga ttaaatcaga       8880
acgcagaagc ggtctgataa aacagaattt gcctggcggc agtagcgcgg tggtcccacc       8940
tgaccccatg ccgaactcag aagtgaaacg ccgtagcgcc gatggtagtg tggggtctcc       9000
ccatgcgaga gtagggaact gccaggcatc aaataaaacg aaaggctcag tcgaaagact       9060
gggcctttcg ttttatctgt tgtttgtcgg tgaacgctct cctgagtagg acaaatccgc       9120
cgggagcgga tttgaacgtt gcgaagcaac ggcccggagg gtggcgggca ggacgcccgc       9180
cataaactgc caggcatcaa attaagcaga aggccatcct gacggatggc cttttttgcgt       9240 ttctacaaac tct                                                         9253
```

<210> SEQ ID NO 8
<211> LENGTH: 4760
<212> TYPE: DNA
<213> ORGANISM: Artificial Sequence
<220> FEATURE:
<223> OTHER INFORMATION: Description of Artificial Sequence: Synthetic "MEVT" operon nucleotide sequence

<400> SEQUENCE: 8

```
gacgcttttt atcgcaactc tctactgttt ctccataccc gtttttttgg gctagcagga         60
ggaattcacc atggtacccg gggatcctct agagtcgact aggaggaata taaaatgaaa       120
aattgtgtca tcgtcagtgc ggtacgtact gctatcggta gttttaacgg ttcactcgct       180
tccaccagcg ccatcgacct gggggcgaca gtaattaaag ccgccattga acgtgcaaaa       240
atcgattcac aacacgttga tgaagtgatt atgggtaacg tgttacaagc cgggctgggg       300
caaaatccgg cgcgtcaggc actgttaaaa gcgggctgg cagaaacggt gtgcggattc       360
acggtcaata aagtatgtgg ttcgggtctt aaaagtgtgg cgcttgccgc ccaggccatt       420
caggcaggtc aggcgcagag cattgtggcg ggggtatgg aaaatatgag tttagccccc       480
tacttactcg atgcaaaagc acgctctggt tatcgtcttg gagacggaca ggtttatgac       540
```

```
gtaatcctgc gcgatggcct gatgtgcgcc acccatggtt atcatatggg gattaccgcc    600
gaaaacgtgg ctaaagagta cggaattacc cgtgaaatgc aggatgaact ggcgctacat    660
tcacagcgta aagcggcagc cgcaattgag tccggtgctt ttacagccga aatcgtcccg    720
gtaaatgttg tcactcgaaa gaaaaccttc gtcttcagtc aagacgaatt cccgaaagcg    780
aattcaacgg ctgaagcgtt aggtgcattg cgcccggcct tcgataaagc aggaacagtc    840
accgctggga acgcgtctgg tattaacgac ggtgctgccg ctctggtgat tatggaagaa    900
tctgcggcgc tggcagcagg ccttaccccc tggctcgca ttaaaagtta tgccagcggt     960
ggcgtgcccc ccgcattgat gggtatgggg ccagtacctg ccacgcaaaa agcgttacaa   1020
ctggcggggc tgcaactggc ggatattgat ctcattgagg ctaatgaagc atttgctgca   1080
cagttccttg ccgttgggaa aaacctgggc tttgattctg agaaagtgaa tgtcaacggc   1140
ggggccatcg cgctcgggca tcctatcggt gccagtggtg ctcgtattct ggtcacacta   1200
ttacatgcca tgcaggcacg cgataaaacg ctggggctgg caacactgtg cattggcggc   1260
ggtcagggaa ttgcgatggt gattgaacgg ttgaattaag gaggacagct aaatgaaact   1320
ctcaactaaa ctttgttggt gtggtattaa aggaagactt aggccgcaaa agcaacaaca   1380
attacacaat acaaacttgc aaatgactga actaaaaaaa caaagaccg ctgaacaaaa    1440
aaccagacct caaaatgtcg gtattaaagg tatccaaatt tacatcccaa ctcaatgtgt   1500
caaccaatct gagctagaga aatttgatgg cgtttctcaa ggtaaataca caattggtct   1560
gggccaaacc aacatgtctt ttgtcaatga cagagaagat atctactcga tgtccctaac   1620
tgttttgtct aagttgatca agagttacaa catcgacacc aacaaaattg gtagattaga   1680
agtcggtact gaaactctga ttgacaagtc caagtctgtc aagtctgtct tgatgcaatt   1740
gtttggtgaa acactgacg tcgaaggtat tgacacgctt aatgcctgtt acggtggtac    1800
caacgcgttg ttcaactctt tgaactggat tgaatctaac gcatgggatg gtagagacgc   1860
cattgtagtt tgcggtgata ttgccatcta cgataagggt gccgcaagac caaccggtgg   1920
tgccggtact gttgctatgt ggatcggtcc tgatgctcca attgtatttg actctgtaag   1980
agcttcttac atggaacacg cctacgattt ttacaagcca gatttcacca gcgaatatcc   2040
ttacgtcgat ggtcattttt cattaacttg ttacgtcaag gctcttgatc aagtttacaa   2100
gagttattcc aagaaggcta tttctaaagg gttggttagc gatcccgctg gttcggatgc   2160
tttgaacgtt ttgaaatatt tcgactacaa cgttttccat gttccaacct gtaaattggt   2220
cacaaaatca tacggtagat tactatataa cgatttcaga gccaatcctc aattgttccc   2280
agaagttgac gccgaattag ctactcgcga ttatgacgaa tctttaaccg ataagaacat   2340
tgaaaaaact tttgttaatg ttgctaagcc attccacaaa gagagagttg cccaatcttt   2400
gattgttcca acaaacacag gtaacatgta caccgcatct gtttatgccg cctttgcatc   2460
tctattaaac tatgttggat ctgacgactt acaaggcaag cgtgttggtt tattttctta   2520
cggttccgt ttagctgcat ctctatattc ttgcaaaatt gttggtgacg tccaacatat    2580
tatcaaggaa ttagatatta ctaacaaatt agccaagaga atcaccgaaa ctccaaagga   2640
ttacgaagct gccatcgaat tgagagaaaa atgcccattt gaagaagaact tcaaacctca   2700
aggttccatt gagcatttgc aaagtggtgt ttactacttg accaacatcg atgacaaatt   2760
tagaagatct tacgatgtta aaaataagg aggattacac tatggtttta accaataaaa    2820
cagtcatttc tggatcgaaa gtcaaaagtt tatcatctgc gcaatcgagc tcatcaggac   2880
```

-continued

```
cttcatcatc tagtgaggaa gatgattccc gcgatattga aagcttggat aagaaaatac      2940
gtcctttaga agaattagaa gcattattaa gtagtggaaa tacaaaacaa ttgaagaaca      3000
aagaggtcgc tgccttggtt attcacggta agttaccttt gtacgctttg gagaaaaaat      3060
taggtgatac tacgagagcg gttgcggtac gtaggaaggc tctttcaatt ttggcagaag      3120
ctcctgtatt agcatctgat cgtttaccat ataaaaatta tgactacgac cgcgtatttg      3180
gcgcttgttg tgaaaatgtt ataggttaca tgcctttgcc cgttggtgtt ataggcccct      3240
tggttatcga tggtacatct tatcatatac caatggcaac tacagagggt tgtttggtag      3300
cttctgccat gcgtggctgt aaggcaatca atgctggcgg tggtgcaaca actgttttaa      3360
ctaaggatgg tatgacaaga ggcccagtag tccgtttccc aactttgaaa agatctggtg      3420
cctgtaagat atggttagac tcagaagagg gacaaaacgc aattaaaaaa gcttttaact      3480
ctacatcaag atttgcacgt ctgcaacata ttcaaacttg tctagcagga gatttactct      3540
tcatgagatt tagaacaact actggtgacg caatgggtat gaatatgatt tctaaaggtg      3600
tcgaatactc attaaagcaa atggtagaag agtatggctg ggaagatatg gaggttgtct      3660
ccgtttctgg taactactgt accgacaaaa aaccagctgc catcaactgg atcgaaggtc      3720
gtggtaagag tgtcgtcgca gaagctacta ttcctggtga tgttgtcaga aaagtgttaa      3780
aaagtgatgt ttccgcattg gttgagttga acattgctaa gaatttggtt ggatctgcaa      3840
tggctgggtc tgttggtgga tttaacgcac atgcagctaa tttagtgaca gctgttttct      3900
tggcattagg acaagatcct gcacaaaatg ttgaaagttc caactgtata acattgatga      3960
aagaagtgga cggtgatttg agaatttccg tatccatgcc atccatcgaa gtaggtacca      4020
tcggtggtgg tactgttcta gaaccacaag gtgccatgtt ggacttatta ggtgtaagag      4080
gcccgcatgc taccgctcct ggtaccaacg cacgtcaatt agcaagaata gttgcctgtg      4140
ccgtcttggc aggtgaatta tccttatgtg ctgccctagc agccggccat ttggttcaaa      4200
gtcatatgac ccacaacagg aaacctgctg aaccaacaaa acctaacaat ttggacgcca      4260
ctgatataaa tcgtttgaaa gatgggtccg tcacctgcat taaatcctaa gtcgacctgc      4320
aggcatgcaa gcttggctgt tttggcggat gagagaagat tttcagcctg atacagatta      4380
aatcagaacg cagaagcggt ctgataaaac agaatttgcc tggcggcagt agcgcggtgg      4440
tcccacctga ccccatgccg aactcagaag tgaaacgccg tagcgccgat ggtagtgtgg      4500
ggtctcccca tgcgagagta gggaactgcc aggcatcaaa taaaacgaaa ggctcagtcg      4560
aaagactggg cctttcgttt tatctgttgt ttgtcggtga acgctctcct gagtaggaca      4620
aatccgccgg gagcggattt gaacgttgcg aagcaacggc ccggagggtg cgggcagga      4680 cgcccgccat aaactgccag gcatcaaatt aagcagaagg ccatcctgac ggatggcctt      4740
tttgcgtttc tacaaactct                                                 4760
```

<210> SEQ ID NO 9
<211> LENGTH: 4482
<212> TYPE: DNA
<213> ORGANISM: Artificial Sequence
<220> FEATURE:
<223> OTHER INFORMATION: Description of Artificial Sequence: Synthetic "MEVB" operon nucleotide sequence

<400> SEQUENCE: 9

```
gcgcaacgca attaatgtga gttagctcac tcattaggca ccccaggctt tacactttat        60
gcttccggct cgtatgttgt gtggaattgt gagcggataa caatttcaca caggaaacag       120
```

```
ctatgaccat gattacgcca agcgcgcaat taaccctcac taaagggaac aaaagctggg    180
taccgggccc cccctcgagg tcgacggtat cgataagctt gatatcgaat tcctgcagta    240
ggaggaatta accatgtcat taccgttctt aacttctgca ccgggaaagg ttattatttt    300
tggtgaacac tctgctgtgt acaacaagcc tgccgtcgct gctagtgtgt ctgcgttgag    360
aacctacctg ctaataagcg agtcatctgc accagatact attgaattgg acttcccgga    420
cattagcttt aatcataagt ggtccatcaa tgatttcaat gccatcaccg aggatcaagt    480
aaactcccaa aaattggcca aggctcaaca agccaccgat ggcttgtctc aggaactcgt    540
tagtcttttg gatccgttgt tagctcaact atccgaatcc ttccactacc atgcagcgtt    600
ttgtttcctg tatatgtttg tttgcctatg cccccatgcc aagaatatta gtttctttt     660 aaagtctact ttacccatcg gtgctgggtt gggctcaagc gcctctattt ctgtatcact    720
ggccttagct atggcctact tggggggggtt aataggatct aatgacttgg aaaagctgtc    780
agaaaacgat aagcatatag tgaatcaatg ggccttcata ggtgaaaagt gtattcacgg    840
taccccttca ggaatagata acgctgtggc cacttatggt aatgccctgc tatttgaaaa    900
agactcacat aatggaacaa taaacacaaa caatttttaag ttcttagatg atttcccagc    960
cattccaatg atcctaacct atactagaat tccaaggtct acaaaagatc ttgttgctcg   1020
cgttcgtgtg ttggtcaccg agaaatttcc tgaagttatg aagccaattc tagatgccat   1080
gggtgaatgt gccctacaag gcttagagat catgactaag ttaagtaaat gtaaaggcac   1140
cgatgacgag gctgtagaaa ctaataatga actgtatgaa caactattgg aattgataag   1200
aataaatcat ggactgcttg tctcaatcgg tgtttctcat cctggattag aacttattaa   1260
aaatctgagc gatgatttga gaattggctc cacaaaactt accggtgctg gtggcggcgg   1320
ttgctctttg actttgttac gaagagacat tactcaagag caaattgaca gcttcaaaaa   1380
gaaattgcaa gatgattta gttacgagac atttgaaaca gacttgggtg ggactggctg    1440
ctgtttgtta agcgcaaaaa atttgaataa agatcttaaa atcaaatccc tagtattcca   1500
attatttgaa aataaaacta ccacaaagca acaaattgac gatctattat tgccaggaaa   1560
cacgaattta ccatggactt cataggaggc agatcaaatg tcagagttga gagccttcag   1620
tgccccaggg aaagcgttac tagctggtgg atatttagtt ttagatacaa aatatgaagc   1680
atttgtagtc ggattatcgg caagaatgca tgctgtagcc catccttacg gttcattgca   1740
agggtctgat aagtttgaag tgcgtgtgaa aagtaaacaa tttaaagatg gggagtggct   1800
gtaccatata agtcctaaaa gtggcttcat tcctgtttcg ataggcggat ctaagaaccc   1860
tttcattgaa aaagttatcg ctaacgtatt tagctacttt aaacctaaca tggacgacta   1920
ctgcaataga aacttgttcg ttattgatat tttctctgat gatgcctacc attctcagga   1980
ggatagcgtt accgaacatc gtggcaacag aagattgagt tttcattcgc acagaattga   2040
agaagttccc aaaacagggc tgggctcctc ggcaggttta gtcacagttt taactacagc   2100
tttggcctcc ttttttgtat cggacctgga aaataatgta gacaaatata gagaagttat   2160
tcataattta gcacaagttg ctcattgtca agctcagggt aaaattggaa gcgggtttga   2220
tgtagcggcg gcagcatatg gatctatcag atatagaaga ttcccacccg cattaatctc   2280
taatttgcca gatattggaa gtgctactta cggcagtaaa ctggcgcatt ggttgatga    2340 agaagactgg aatattacga ttaaaagtaa ccatttacct tcgggattaa ctttatggat   2400
gggcgatatt aagaatggtt cagaaacagt aaaactggtc cagaaggtaa aaaattggta   2460
tgattcgcat atgccagaaa gcttgaaaat atatacagaa ctcgatcatg caaattctag   2520
```

```
atttatggat ggactatcta aactagatcg cttacacgag actcatgacg attacagcga   2580
tcagatattt gagtctcttg agaggaatga ctgtacctgt caaaagtatc ctgaaatcac   2640
agaagttaga gatgcagttg ccacaattag acgttccttt agaaaaataa ctaagaatc    2700 tggtgccgat atcgaacctc ccgtacaaac tagcttattg gatgattgcc agaccttaaa   2760
aggagttctt acttgcttaa tacctggtgc tggtggttat gacgccattg cagtgattac   2820
taagcaagat gttgatctta gggctcaaac cgctaatgac aaaagatttt ctaaggttca   2880
atggctggat gtaactcagg ctgactgggg tgttaggaaa gaaaaagatc cggaaactta   2940
tcttgataaa taggaggtaa tactcatgac cgtttacaca gcatccgtta ccgcacccgt   3000
caacatcgca acccttaagt attgggggaa aagggacacg aagttgaatc tgcccaccaa   3060
ttcgtccata tcagtgactt tatcgcaaga tgacctcaga acgttgacct ctgcggctac   3120
tgcacctgag tttgaacgcg acactttgtg gttaaatgga gaaccacaca gcatcgacaa   3180
tgaaagaact caaaattgtc tgcgcgacct acgccaatta agaaaggaaa tggaatcgaa   3240
ggacgcctca ttgcccacat tatctcaatg gaaactccac attgtctccg aaaataactt   3300
tcctacagca gctggtttag cttcctccgc tgctggcttt gctgcattgg tctctgcaat   3360
tgctaagtta taccaattac cacagtcaac ttcagaaata tctagaatag caagaaaggg   3420
gtctggttca gcttgtagat cgttgtttgg cggatacgtg gcctgggaaa tgggaaaagc   3480
tgaagatggt catgattcca tggcagtaca aatcgcagac agctctgact ggcctcagat   3540
gaaagcttgt gtcctagttg tcagcgatat taaaaaggat gtgagttcca ctcagggtat   3600
gcaattgacc gtggcaacct ccgaactatt taaagaaaga attgaacatg tcgtaccaaa   3660
gagatttgaa gtcatgcgta aagccattgt tgaaaaagat ttcgccacct ttgcaaagga   3720
aacaatgatg gattccaact ctttccatgc cacatgtttg gactctttcc ctccaatatt   3780
ctacatgaat gacacttcca agcgtatcat cagttggtgc cacaccatta atcagtttta   3840
cggagaaaca atcgttgcat acacgtttga tgcaggtcca aatgctgtgt tgtactactt   3900
agctgaaaat gagtcgaaac tctttgcatt tatctataaa ttgtttggct ctgttcctgg   3960
atgggacaag aaatttacta ctgagcagct tgaggctttc aaccatcaat tgaatcatc    4020 taactttact gcacgtgaat tggatcttga gttgcaaaag gatgttgcca gagtgatttt   4080
aactcaagtc ggttcaggcc cacaagaaac aaacgaatct ttgattgacg caaagactgg   4140
tctaccaaag gaataactgc agcccggggg atccactagt tctagagcgg ccgccaccgc   4200
ggtggagctc caattcgccc tatagtgagt cgtattacgc gcgctcactg gccgtcgttt   4260
tacaacgtcg tgactgggaa aaccctggcg ttacccaact taatcgcctt gcagcacatc   4320
cccctttcgc cagctggcgt aatagcgaag aggcccgcac cgatcgccct tcccaacagt   4380
tgcgcagcct gaatggcgaa tggaaattgt aagcgttaat attttgttaa aattcgcgtt   4440
aaatttttgt taaatcagct catttttaa ccaataggcc ga                      4482
```

<210> SEQ ID NO 10
<211> LENGTH: 549
<212> TYPE: DNA
<213> ORGANISM: Artificial Sequence
<220> FEATURE:
<223> OTHER INFORMATION: Description of Artificial Sequence: Synthetic
      Isopentenyl pyrophosphate isomerase (idi)
      nucleotide sequence

<400> SEQUENCE: 10

```
atgcaaacgg aacacgtcat tttattgaat gcacagggag ttcccacggg tacgctggaa    60
aagtatgccg cacacacggc agacacccgc ttacatctcg cgttctccag ttggctgttt   120
aatgccaaag acaattatt agttacccgc cgcgcactga gcaaaaaagc atggcctggc   180
gtgtggacta actcggtttg tgggcaccca caactgggag aaagcaacga agacgcagtg   240
atccgccgtt gccgttatga gcttggcgtg gaaattacgc ctcctgaatc tatctatcct   300
gactttcgct accgcgccac cgatccgagt ggcattgtgg aaaatgaagt gtgtccggta   360
tttgccgcac gcaccactag tgcgttacag atcaatgatg atgaagtgat ggattatcaa   420
tggtgtgatt tagcagatgt attacacggt attgatgcca cgccgtgggc gttcagtccg   480
tggatggtga tgcaggcgac aaatcgcgaa gccagaaaac gattatctgc atttacccag   540
cttaaataa                                                            549

<210> SEQ ID NO 11
<211> LENGTH: 900
<212> TYPE: DNA
<213> ORGANISM: Artificial Sequence
<220> FEATURE:
<223> OTHER INFORMATION: Description of Artificial Sequence: Synthetic
      Farnesyl pyrophosphate synthase (ispA) nucleotide
      sequence

<400> SEQUENCE: 11
atggactttc gcagcaact cgaagcctgc gttaagcagg ccaaccaggc gctgagccgt    60
tttatcgccc cactgcccctt tcagaacact cccgtggtcg aaaccatgca gtatggcgca   120
ttattaggtg gtaagcgcct gcgacctttc ctggtttatg ccaccggtca tatgttcggc   180
gttagcacaa acacgctgga cgcacccgct gccgccgttg agtgtatcca cgcttactca   240
ttaattcatg atgatttacc ggcaatggat gatgacgatc tgcgtcgcgg tttgccaacc   300
tgccatgtga gtttggcga agcaaacgcg attctcgctg gcgacgcttt acaaacgctg   360
gcgttctcga ttttaagcga tgccgatatg ccggaagtgt cggaccgcga cagaatttcg   420
atgatttctg aactggcgag cgccagtggt attgccggaa tgtgcggtgg tcaggcatta   480
gatttagacg cggaaggcaa acacgtacct ctggacgcgc ttgagcgtat tcatcgtcat   540
aaaaccggcg cattgattcg cgccgccgtt cgccttggtg cattaagcgc cggagataaa   600
ggacgtcgtg ctctgccggt actcgacaag tatgcagaga gcatcggcct tgccttccag   660
gttcaggatg acatcctgga tgtggtggga gatactgcaa cgttgggaaa acgccagggt   720
gccgaccagc aacttggtaa agtacctac cctgcacttc tgggtcttga gcaagcccgg   780
aagaaagccc gggatctgat cgacgatgcc cgtcagtcgc tgaaacaact ggctgaacag   840
tcactcgata cctcggcact ggaagcgcta gcggactaca tcatccagcg taataaataa   900

<210> SEQ ID NO 12
<211> LENGTH: 5051
<212> TYPE: DNA
<213> ORGANISM: Artificial Sequence
<220> FEATURE:
<223> OTHER INFORMATION: Description of Artificial Sequence: Synthetic
      "MBI" operon nucleotide sequence

<400> SEQUENCE: 12
gcgcaacgca attaatgtga gttagctcac tcattaggca ccccaggctt tacactttat    60
gcttccggct cgtatgttgt gtggaattgt gagcggataa caatttcaca caggaaacag   120
ctatgaccat gattacgcca agcgcgcaat taaccctcac taaagggaac aaaagctggg   180
```

```
taccgggccc ccccteogagg tcgacggtat cgataagett gatategaat tcctgcagta    240
ggaggaatta accatgtcat taccgttctt aacttctgca ccgggaaagg ttattatttt    300
tggtgaacac tctgctgtgt acaacaagcc tgccgtcgct gctagtgtgt ctgcgttgag    360
aacctacctg ctaataagcg agtcatctgc accagatact attgaattgg acttcccgga    420
cattagcttt aatcataagt ggtccatcaa tgatttcaat gccatcaccg aggatcaagt    480
aaactcccaa aaattggcca aggctcaaca agccaccgat ggcttgtctc aggaactcgt    540
tagtcttttg gatccgttgt tagctcaact atccgaatcc ttccactacc atgcagcgtt    600
ttgtttcctg tatatgtttg tttgcctatg cccccatgcc aagaatatta agttttcttt    660
aaagtctact ttaccatcg gtgctgggtt gggctcaagc gcctctattt ctgtatcact    720
ggccttagct atggcctact tggggggtt aataggatct aatgacttgg aaaagctgtc    780
agaaaacgat aagcatatag tgaatcaatg gccttcata ggtgaaaagt gtattcacgg    840
tacccttca ggaatagata cgctgtggc cacttatggt aatgccctgc tatttgaaaa    900
agactcacat aatggaacaa taaacacaaa caattttaag ttcttagatg atttcccagc    960
cattccaatg atcctaacct atactagaat tccaaggtct acaaaagatc ttgttgctcg   1020
cgttcgtgtg ttggtcaccg agaaatttcc tgaagttatg aagccaattc tagatgccat   1080
gggtgaatgt gccctacaag gcttagagat catgactaag ttaagtaaat gtaaaggcac   1140
cgatgacgag gctgtagaaa ctaataatga actgtatgaa caactattgg aattgataag   1200
aataaatcat ggactgcttg tctcaatcgg tgtttctcat cctggattag aacttattaa   1260
aaatctgagc gatgatttga gaattggctc cacaaaactt accggtgctg gtggcggcgg   1320
ttgctctttg actttgttac gaagagacat tactcaagag caaattgaca gcttcaaaaa   1380
gaaattgcaa gatgatttta gttacgagac atttgaaaca gacttgggtg ggactggctg   1440
ctgtttgtta agcgcaaaaa atttgaataa agatcttaaa atcaaatccc tagtattcca   1500
attatttgaa ataaaaacta ccacaaagca acaaattgac gatctattat tgccaggaaa   1560
cacgaattta ccatggactt cataggaggc agatcaaatg tcagagttga gagccttcag   1620
tgccccaggg aaagcgttac tagctggtgg atatttagtt ttagatacaa aatatgaagc   1680
atttgtagtc ggattatcgg caagaatgca tgctgtagcc catccttacg gttcattgca   1740
agggtctgat aagtttgaag tgcgtgtgaa aagtaaacaa tttaaagatg gggagtggct   1800
gtaccatata agtcctaaaa gtggcttcat tcctgtttcg ataggcggat ctaagaaccc   1860
tttcattgaa aaagttatcg ctaacgtatt tagctacttt aaacctaaca tggacgacta   1920
ctgcaataga aacttgttcg ttattgatat tttctctgat gatgcctacc attctcagga   1980
ggatagcgtt accgaacatc gtggcaacag aagattgagt tttcattcgc acagaattga   2040
agaagttccc aaaacagggc tgggctcctc ggcaggttta gtcacagttt taactacagc   2100
tttggcctcc ttttttgtat cggacctgga aaataatgta gacaaatata gagaagttat   2160
tcataattta gcacaagttg ctcattgtca agctcagggt aaaattggaa gcgggtttga   2220
tgtagcggcg gcagcatatg gatctatcag atatagaaga ttcccacccg cattaatctc   2280
taatttgcca gatattggaa gtgctactta cggcagtaaa ctggcgcatt tggttgatga   2340
agaagactgg aatattacga ttaaaagtaa ccatttacct tcgggattaa ctttatggat   2400
gggcgatatt aagaatggtt cagaaacagt aaaactggtc cagaaggtaa aaaattggta   2460
tgattcgcat atgccagaaa gcttgaaaat atatacagaa ctcgatcatg caaattctag   2520
atttatggat ggactatcta aactagatcg cttacacgag actcatgacg attacagcga   2580
```

```
tcagatattt gagtctcttg agaggaatga ctgtacctgt caaaagtatc ctgaaatcac    2640
agaagttaga gatgcagttg ccacaattag acgttccttt agaaaaataa ctaaagaatc    2700
tggtgccgat atcgaacctc ccgtacaaac tagcttattg gatgattgcc agaccttaaa    2760
aggagttctt acttgcttaa tacctggtgc tggtggttat gacgccattg cagtgattac    2820
taagcaagat gttgatctta gggctcaaac cgctaatgac aaaagatttt ctaaggttca    2880
atggctggat gtaactcagg ctgactgggg tgttaggaaa gaaaaagatc cggaaactta    2940
tcttgataaa taggaggtaa tactcatgac cgtttacaca gcatccgtta ccgcacccgt    3000
caacatcgca acccttaagt attggggaa aagggacacg aagttgaatc tgcccaccaa    3060
ttcgtccata tcagtgactt tatcgcaaga tgacctcaga acgttgacct ctgcggctac    3120
tgcacctgag tttgaacgcg acactttgtg gttaaatgga gaaccacaca gcatcgacaa    3180
tgaaagaact caaaattgtc tgcgcgacct acgccaatta agaaaggaaa tggaatcgaa    3240
ggacgcctca ttgcccacat tatctcaatg gaaactccac attgtctccg aaaataactt    3300
tcctacagca gctggtttag cttcctccgc tgctggcttt gctgcattgg tctctgcaat    3360
tgctaagtta taccaattac cacagtcaac ttcagaaata tctagaatag caagaaaggg    3420
gtctggttca gcttgtagat cgttgtttgg cggatacgtg gcctgggaaa tgggaaaagc    3480
tgaagatggt catgattcca tggcagtaca atcgcagac agctctgact ggcctcagat    3540
gaaagcttgt gtcctagttg tcagcgatat taaaaaggat gtgagttcca ctcagggtat    3600
gcaattgacc gtggcaacct ccgaactatt taaagaaaga attgaacatg tcgtaccaaa    3660
gagatttgaa gtcatgcgta aagccattgt tgaaaaagat ttcgccacct ttgcaaagga    3720
aacaatgatg gattccaact ctttccatgc cacatgtttg gactctttcc ctccaatatt    3780
ctacatgaat gacacttcca agcgtatcat cagttggtgc cacaccatta atcagtttta    3840
cggagaaaca atcgttgcat acacgtttga tgcaggtcca aatgctgtgt tgtactactt    3900
agctgaaaat gagtcgaaac tctttgcatt tatctataaa ttgtttggct ctgttcctgg    3960
atgggacaag aaatttacta ctgagcagct tgaggctttc aaccatcaat ttgaatcatc    4020
taactttact gcacgtgaat tggatcttga gttgcaaaag gatgttgcca gagtgatttt    4080
aactcaagtc ggttcaggcc cacaagaaac aaacgaatct ttgattgacg caaagactgg    4140
tctaccaaag gaataactgc agcccgggag gaggattact atatgcaaac ggaacacgtc    4200
attttattga atgcacaggg agttcccacg ggtacgctgg aaaagtatgc cgcacacacg    4260
gcagacaccc gcttacatct cgcgttctcc agttggctgt taatgccaa aggacaatta    4320 ttagttaccc gccgcgcact gagcaaaaaa gcatggcctg gcgtgtggac taactcggtt    4380
tgtgggcacc cacaactggg agaaagcaac gaagacgcag tgatccgccg ttgccgttat    4440
gagcttggcg tggaaattac gcctcctgaa tctatctatc ctgactttcg ctaccgcgcc    4500
accgatccga gtggcattgt ggaaaatgaa gtgtgtccgg tatttgccgc acgcaccact    4560
agtgcgttac agatcaatga tgatgaagtg atggattatc aatggtgtga tttagcagat    4620
gtattacacg gtattgatgc cacgccgtgg gcgttcagtc cgtggatggt gatgcaggcg    4680
acaaatcgcg aagccagaaa acgattatct gcatttaccc agcttaaaata acccggggga    4740 tccactagtt ctagagcggc cgccaccgcg gtggagctcc aattcgccct atagtgagtc    4800
gtattacgcg cgctcactgg ccgtcgtttt acaacgtcgt gactgggaaa accctggcgt    4860
tacccaactt aatcgccttg cagcacatcc cccttcgcc agctggcgta atagcgaaga    4920
```

```
ggcccgcacc gatcgccctt cccaacagtt gcgcagcctg aatggcgaat ggaaattgta    4980
agcgttaata ttttgttaaa attcgcgtta aatttttgtt aaatcagctc atttttttaac   5040 caataggccg a                                                         5051
```

<210> SEQ ID NO 13
<211> LENGTH: 5963
<212> TYPE: DNA
<213> ORGANISM: Artificial Sequence
<220> FEATURE:
<223> OTHER INFORMATION: Description of Artificial Sequence: Synthetic
      "MBIS" operon nucleotide sequence

<400> SEQUENCE: 13

```
gcgcaacgca attaatgtga gttagctcac tcattaggca ccccaggctt tacactttat     60
gcttccggct cgtatgttgt gtggaattgt gagcggataa caatttcaca caggaaacag    120
ctatgaccat gattacgcca agcgcgcaat taaccctcac taaagggaac aaaagctggg    180
taccgggccc cccctcgagg tcgacggtat cgataagctt gatatcgaat tcctgcagta    240
ggaggaatta accatgtcat taccgttctt aacttctgca ccgggaaagg ttattatttt    300
tggtgaacac tctgctgtgt acaacaagcc tgccgtcgct gctagtgtgt ctgcgttgag    360
aacctacctg ctaataagcg agtcatctgc accagatact attgaattgg acttcccgga    420
cattagcttt aatcataagt ggtccatcaa tgatttcaat gccatcaccg aggatcaagt    480
aaactcccaa aaattggcca aggctcaaca agccaccgat ggcttgtctc aggaactcgt    540
tagtcttttg gatccgttgt tagctcaact atccgaatcc ttccactacc atgcagcgtt    600
ttgtttcctg tatatgtttg tttgcctatg ccccatgcc aagaatatta agttttcttt    660
aaagtctact ttacccatcg gtgctgggtt gggctcaagc gcctctattt ctgtatcact    720
ggccttagct atggcctact tgggggggtt aataggatct aatgacttgg aaaagctgtc    780
agaaaacgat aagcatatag tgaatcaatg gccttcata ggtgaaaagt gtattcacgg    840
taccccttca ggaatagata cgctgtggc cacttatggt aatgccctgc tatttgaaaa    900
agactcacat aatggaacaa taaacacaaa caatttaag ttcttagatg atttcccagc    960
cattccaatg atcctaacct atactagaat tccaaggtct acaaaagatc ttgttgctcg   1020
cgttcgtgtg ttggtcaccg agaaatttcc tgaagttatg aagccaattc tagatgccat   1080
gggtgaatgt gccctacaag gcttagagat catgactaag ttaagtaaat gtaaaggcac   1140
cgatgacgag gctgtagaaa ctaataatga actgtatgaa caactattgg aattgataag   1200
aataaatcat ggactgcttg tctcaatcgg tgtttctcat cctggattag aacttattaa   1260
aaatctgagc gatgatttga gaattggctc cacaaaactt accggtgctg gtggcggcgg   1320
ttgctctttg actttgttac gaagagacat tactcaagag caaattgaca gcttcaaaaa   1380
gaaattgcaa gatgatttta gttacgagac atttgaaaca gacttgggtg ggactggctg   1440
ctgtttgtta agcgcaaaaa atttgaataa agatcttaaa atcaaatccc tagtattcca   1500
attatttgaa aataaaacta ccacaaagca acaaattgac gatctattat tgccaggaaa   1560
cacgaattta ccatggactt cataggaggc agatcaaatg tcagagttga gagccttcag   1620
tgccccaggg aaagcgttac tagctggtgg atatttagtt ttagatacaa atatgaagc    1680 atttgtagtc ggattatcgg caagaatgca tgctgtagcc catccttacg gttcattgca   1740
agggtctgat aagtttgaag tgcgtgtgaa agtaaacaa tttaaagatg gggagtggct    1800
gtaccatata agtcctaaaa gtggcttcat tcctgtttcg ataggcggat ctaagaaccc   1860
```

```
tttcattgaa aaagttatcg ctaacgtatt tagctacttt aaacctaaca tggacgacta    1920
ctgcaataga aacttgttcg ttattgatat tttctctgat gatgcctacc attctcagga    1980
ggatagcgtt accgaacatc gtggcaacag aagattgagt tttcattcgc acagaattga    2040
agaagttccc aaaacagggc tgggctcctc ggcaggttta gtcacagttt taactacagc    2100
tttggcctcc ttttttgtat cggacctgga aaataatgta gacaaatata gagaagttat    2160
tcataattta gcacaagttg ctcattgtca agctcagggt aaaattggaa gcgggtttga    2220
tgtagcggcg gcagcatatg gatctatcag atatagaaga ttcccacccg cattaatctc    2280
taatttgcca gatattggaa gtgctactta cggcagtaaa ctggcgcatt tggttgatga    2340
agaagactgg aatattacga ttaaaagtaa ccatttacct tcgggattaa ctttatggat    2400
gggcgatatt aagaatggtt cagaaacagt aaaactggtc cagaaggtaa aaattggta    2460 tgattcgcat atgccagaaa gcttgaaaat atatacagaa ctcgatcatg caaattctag    2520
atttatggat ggactatcta aactagatcg cttacacgag actcatgacg attacagcga    2580
tcagatattt gagtctcttg agaggaatga ctgtacctgt caaaagtatc ctgaaatcac    2640
agaagttaga gatgcagttg ccacaattag acgttccttt agaaaaataa ctaaagaatc    2700
tggtgccgat atcgaaccct ccgtacaaac tagcttattg gatgattgcc agaccttaaa    2760
aggagttctt acttgcttaa tacctggtgc tggtggttat gacgccattg cagtgattac    2820
taagcaagat gttgatctta gggctcaaac cgctaatgac aaaagatttt ctaaggttca    2880
atggctggat gtaactcagg ctgactgggg tgttaggaaa gaaaaagatc cggaaactta    2940
tcttgataaa taggaggtaa tactcatgac cgtttacaca gcatccgtta ccgcacccgt    3000
caacatcgca acccttaagt attgggggaa aagggacacg aagttgaatc tgcccaccaa    3060
ttcgtccata tcagtgactt tatcgcaaga tgacctcaga acgttgacct ctgcggctac    3120
tgcacctgag tttgaacgcg acactttgtg gttaaatgga gaaccacaca gcatcgacaa    3180
tgaaagaact caaaattgtc tgcgcgacct acgccaatta agaaaggaaa tggaatcgaa    3240
ggacgcctca ttgcccacat tatctcaatg gaaactccac attgtctccg aaaataactt    3300
tcctacagca gctggtttag cttcctccgc tgctggcttt gctgcattgg tctctgcaat    3360
tgctaagtta taccaattac cacagtcaac ttcagaaata tctagaatag caagaaaggg    3420
gtctggttca gcttgtagat cgttgtttgg cggatacgtg gcctgggaaa tgggaaaagc    3480
tgaagatggt catgattcca tggcagtaca aatcgcagac agctctgact ggcctcagat    3540
gaaagcttgt gtcctagttg tcagcgatat taaaaaggat gtgagttcca ctcagggtat    3600
gcaattgacc gtggcaacct ccgaactatt taaagaaaga attgaacatg tcgtaccaaa    3660
gagatttgaa gtcatgcgta aagccattgt tgaaaaagat ttcgccacct ttgcaagga    3720 aacaatgatg gattccaact ctttccatgc cacatgtttg gactctttcc ctccaatatt    3780
ctacatgaat gacacttcca gcgtatcat cagttggtgc cacaccatta atcagttta    3840 cggagaaaca atcgttgcat acacgtttga tgcaggtcca aatgctgtgt tgtactactt    3900
agctgaaaat gagtcgaaac tctttgcatt tatctataaa ttgtttggct ctgttcctgg    3960
atgggacaag aaatttacta ctgagcagct tgaggctttc aaccatcaat tgaatcatc    4020 taactttact gcacgtgaat tggatcttga gttgcaaaag gatgttgcca gagtgatttt    4080
aactcaagtc ggttcaggcc cacaagaaac aaacgaatct ttgattgacg caaagactgg    4140
tctaccaaag gaataactgc agcccgggag gaggattact atatgcaaac ggaacacgtc    4200
attttattga atgcacaggg agttcccacg ggtacgctgg aaaagtatgc cgcacacacg    4260
```

```
gcagacaccc gcttacatct cgcgttctcc agttggctgt ttaatgccaa aggacaatta      4320
ttagttaccc gccgcgcact gagcaaaaaa gcatggcctg gcgtgtggac taactcggtt      4380
tgtgggcacc cacaactggg agaaagcaac gaagacgcag tgatccgccg ttgccgttat      4440
gagcttggcg tggaaattac gcctcctgaa tctatctatc ctgactttcg ctaccgcgcc      4500
accgatccga gtggcattgt ggaaaatgaa gtgtgtccgg tatttgccgc acgcaccact      4560
agtgcgttac agatcaatga tgatgaagtg atggattatc aatggtgtga tttagcagat      4620
gtattacacg gtattgatgc cacgccgtgg gcgttcagtc cgtggatggt gatgcaggcg      4680
acaaatcgcg aagccagaaa acgattatct gcatttaccc agcttaaata acccggggga      4740
tccactagtt ctagagcggc cgccaccgcg gaggaggaat gagtaatgga ctttccgcag      4800
caactcgaag cctgcgttaa gcaggccaac caggcgctga gccgttttat cgccccactg      4860 cccttcaga acactcccgt ggtcgaaacc atgcagtatg gcgcattatt aggtggtaag      4920
cgcctgcgac ctttcctggt ttatgccacc ggtcatatgt tcggcgttag cacaaacacg      4980
ctggacgcac ccgctgccgc cgttgagtgt atccacgctt actcattaat tcatgatgat      5040
ttaccggcaa tggatgatga cgatctgcgt cgcggtttgc caacctgcca tgtgaagttt      5100
ggcgaagcaa acgcgattct cgctggcgac gctttacaaa cgctggcgtt ctcgatttta      5160
agcgatgccg atatgccgga agtgtcggac cgcgacagaa tttcgatgat ttctgaactg      5220
gcgagcgcca gtggtattgc cggaatgtgc ggtggtcagg cattagattt agacgcggaa      5280
ggcaaacacg tacctctgga cgcgcttgag cgtattcatc gtcataaaac cggcgcattg      5340
attcgcgccg ccgttcgcct tggtgcatta agcgccggag ataaaggacg tcgtgctctg      5400
ccggtactcg acaagtatgc agagagcatc ggccttgcct tccaggttca ggatgacatc      5460
ctggatgtgg tgggagatac tgcaacgttg gaaaacgcc agggtgccga ccagcaactt      5520
ggtaaaagta cctaccctgc acttctgggt cttgagcaag cccggaagaa agcccgggat      5580
ctgatcgacg atgcccgtca gtcgctgaaa caactggctg aacagtcact cgatacctcg      5640
gcactggaag cgctagcgga ctacatcatc cagcgtaata aataagagct ccaattcgcc      5700
ctatagtgag tcgtattacg cgcgctcact ggccgtcgtt ttacaacgtc gtgactggga      5760
aaaccctggc gttacccaac ttaatcgcct tgcagcacat cccccttcg ccagctggcg      5820 taatagcgaa gaggcccgca ccgatcgccc ttcccaacag ttgcgcagcc tgaatggcga      5880
atggaaattg taagcgttaa tattttgtta aaattcgcgt taaattttg ttaaatcagc      5940 tcattttta accaataggc cga                                               5963
```